United States Patent [19]

Dondio et al.

[11] Patent Number: 5,731,322

[45] Date of Patent: Mar. 24, 1998

[54] OCTAHYDRO-1H-PYRROLO[3,2-G] AND [2,3-G]ISOQUINOLINE DERIVATIVES

[75] Inventors: Giulio Dondio; Silvano Ronzoni, both of Milan, Italy

[73] Assignee: SmithKline Beecham S.p.A., Milan, Italy

[21] Appl. No.: 591,514

[22] PCT Filed: Jul. 14, 1994

[86] PCT No.: PCT/EP94/02325

§ 371 Date: Apr. 18, 1996

§ 102(e) Date: Apr. 18, 1996

[87] PCT Pub. No.: WO95/04734

PCT Pub. Date: Feb. 16, 1995

[30] Foreign Application Priority Data

Aug. 6, 1993 [IT] Italy ................ MI93A1788 U
Feb. 4, 1994 [IT] Italy ................ MI94A0202 U

[51] Int. Cl.$^6$ .............. A61K 31/535; A61K 31/44; C07D 471/04; C07D 413/12

[52] U.S. Cl. .............. 514/292; 514/232.8; 514/290; 544/126; 546/84; 546/79

[58] Field of Search ............ 546/79, 84; 514/290, 514/292, 232.8; 544/126

[56] References Cited

U.S. PATENT DOCUMENTS 4,260,762  4/1981  Berger et al. .............. 546/84

FOREIGN PATENT DOCUMENTS

WO93/01186  1/1993  WIPO ................ 546/79

Primary Examiner—Alan L. Rotman
Attorney, Agent, or Firm—Charles M. Kinzig; Edward T. Lentz

[57] ABSTRACT

Tricyclic derivatives of octahydroisoquinoline of formula (I), wherein n is zero or 1 and if n is zero, one of X or Y is NH, oxygen or sulphur, and the other is NH, CH or a $R_4$- or $R_5$-substituted carbon atom; if n is 1, then X and Y are both nitrogen, or one of them is nitrogen and the other is CH or an $R_4$- or $R_5$-substituted carbon atom, have selective receptor agonist or antagonist activity, and are of potential therapeutic utility as analgesics or immunomodulating and/or cardiovascular agents.

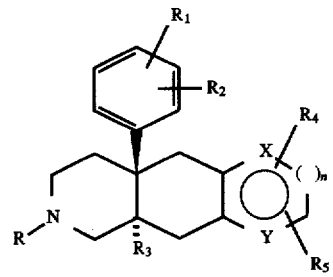

8 Claims, No Drawings

OCTAHYDRO-1H-PYRROLO[3,2-G] AND [2,3-G]ISOQUINOLINE DERIVATIVES

CROSS REFERENCE

This application is a 371 of PCT/EP94/02325 filed Jul. 14, 1994.

This invention is concerned with novel hydroisoquinoline derivatives, processes for their preparation, and their use in medicine. The presence of at least three populations of opioid receptors (μ, δ and kappa) is now well established and documented and all three appear to be present in the central and peripheral nervous system of many species, including man (Lord J. A. H. et al., Nature 1977, 267, 495).

Activation of all 3 opioid receptor subtypes can lead to antinociception in animal models. In particular, studies with peptidic δ agonists have indicated that activation of the δ receptor produces antinociceptive activity in rodents and primates, and can induce clinical analgesia in man (Yaksh T. L. and Onofrio, B. M., Lancet 1983, 1386). Some experiments suggest that these δ analgesics may also lack the usual side-effects associated with δ and kappa receptor activation (Galligan et at. J. Pharm. Exp. Ther. 1984, 229, 641).

Octahydroisoquinoline derivatives having selectivity for the δ receptor have already been described. All the known derivatives are characterized by bicyclic heterocycle systems condensed at the isoquinoline ring. For example, octahydroisoquinoline derivatives are disclosed in EP-A-0, 485,636 (Toray Ind.); JP-A-4,368,384, (Tray Ind.), whereas quinoline- and quinoxaline-octahydroisoquinoline derivatives are disclosed in JP-A-6,275,288 (Toray Ind.). In WO 93/01186 (Dr. Lo Zambeletti), indole-, benzofuro- or quinolinooctahydroisoquinoline derivatives are disclosed.

A structural characteristic of the compounds disclosed in the documents mentioned above, therefore, is the presence of a condensed tetracyclic system.

A novel class of tricyclic derivatives of octahydroisoquinoline condensed with monocyclic heterocycles has now been found, characterised by a selective δ receptor agonistic or antagonistic activity. These derivatives are therefore of potential therapeutic utility as analgesics or immunomodulating and/or cardiovascular agents.

According to the present invention, there is provided a compound, or solvate or salt thereof, of formula (I):

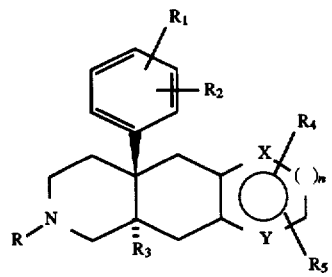

(I)

wherein:

R is hydrogen or a straight or branched $C_1$–$C_5$ alkyl, $C_3$–$C_7$ cycloalkyl, $C_4$–$C_6$ cycloalkylalkyl, $C_3$–$C_5$ alkenyl, aryl, aralkyl or furan-2-yl-alkyl;

$R_1$ and $R_2$, which can be the same or different, are each hydrogen, hydroxy, $C_1$–$C_3$ alkoxy, preferably methoxy, halogen, SH, $C_1$–$C_4$-alkylthio, NHR$_6$, NR$_6$R$_7$, NHCOR$_6$, NHSO$_2$R$_6$, wherein R$_6$ and R$_7$, which are the same or different, are hydrogen or $C_1$–$C_6$ alkyl;

$R_3$ is hydrogen, hydroxy or $C_1$–$C_3$ alkoxy, preferably methoxy;

$R_4$ is a

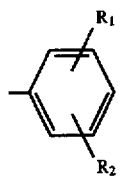

group ($R_1$ and $R_2$ having the meanings defined above) or a —C(Z)—R$_8$ group, in which Z is oxygen or sulphur, and R$_8$ is $C_1$–$C_{18}$-alkyl, $C_1$–$C_{18}$-alkoxy or NR$_9$R$_{10}$, wherein R$_9$ and R$_{10}$, which may be the same or different, are hydrogen, straight or branched $C_1$–$C_6$ alkyl, $C_3$–$C_7$ cycloalkyl, $C_4$–$C_6$ cycloalkylalkyl, $C_3$–$C_6$ alkenyl, aryl, aralkyl or an optionally substituted heterocyclic ring or, taken together with the nitrogen atom which they are linked to, they form an alkylene chain having from 2 to 5 carbon atoms, optionally interrupted by an oxygen or nitrogen atom;

or R$_4$ is a group

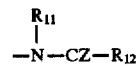

in which R$_{11}$ and R$_{12}$ are the same as R$_9$ and R$_{10}$ respectively, and Z is as defined above;

R$_5$ is hydrogen, $C_1$–$C_{18}$ alkyl, $C_2$–$C_{18}$ alkenyl, trifluoromethyl or is a

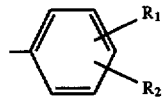

group ($R_1$ and $R_2$ having the meanings defined above);

n is zero or 1;

if n is zero, one of X or Y is NH, oxygen or sulphur, and the other is NH, CH or a R$_4$- or R$_5$-substituted carbon atom; if n is 1, then X and Y are both nitrogen, or one of them is nitrogen and the other is CH or a R$_4$- or R$_5$-substituted carbon atom.

When R is aryl, it is preferably phenyl, and when it is aralkyl, it is preferably phenyl-$C_1$–$C_6$ alkyl.

Examples of R are hydrogen, methyl, ethyl, cyclopropylmethyl, propyl, 2-furylmethyl and 2-phenylethyl.

Examples of $R_1$ and $R_2$ are hydrogen, hydroxy, methoxy, chlorine, bromine, fluorine, SH, methylthio, amino, methylamino, ethylamino, dimethylamino, diethylamino, diisopropylamino, methylisopropylamino, acetylamino and sulfonylamino, at any position of the ring.

Examples of R$_6$ and R$_7$ groups are hydrogen, methyl, ethyl, n-propyl, isopropyl and n-butyl.

Examples of R$_8$ groups are methyl, ethyl, n-propyl, isopropyl, n-butyl, n-pentyl, n-heptyl, n-undecyl, n-tridecyl, n-heptadecyl, methoxy, ethoxy, propoxy, isopropoxy, hexyloxy, decyloxy, amino, methylamino, dimethylamino, diethylamino.

Examples of R$_4$ are ethoxycarbonyl, i-butyloxycarbonyl, aminocarbonyl, dimethylaminocarbonyl, diethylaminocarbonyl, di-n-propylaminocarbonyl, di-i-propylaminocarbonyl, pyrrolidinocarbonyl, benzylaminocarbonyl, phenylaminocarbonyl, morpholinocarbonyl, N-ethyl-N-i-isopropylaminocarbonyl, diethylaminothiocarbonyl, phenyl.

Examples of $R_5$ groups are hydrogen, methyl, ethyl, propyl, butyl, hexyl, octyl, decyl, dodecyl, octadecyl, allyl, trifluoromethyl and phenyl.

Examples of $R_9$ and $R_{10}$ are hydrogen, methyl, ethyl, propyl, isopropyl, butyl, isobutyl, pentyl, allyl, benzyl, phenyl, pyrrole, furan and pyridine.

Examples of the group

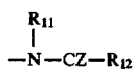

are acetamido, propionamido, isobutyramido and benzamido.

A first group of preferred compounds of formula (I) is one in which n is zero, X is NH and Y is CH or a $R_4$- or $R_5$-substituted carbon atom.

A second group of preferred compounds of formula (I) is one in which n is zero, X is CH or a $R_4$- or $R_5$-substituted carbon atom and Y is NH.

A third group of preferred compounds of formula (I) is one in which n is zero, X is a sulphur or oxygen atom and Y is CH or a $R_4$- or $R_5$-substituted carbon atom.

A fourth group of preferred compounds of formula (I) is one in which n is zero, X is CH or a $R_4$- or $R_5$-substituted carbon atom, and Y is an oxygen or sulphur atom.

A fifth group of preferred compounds of formula (I) is one in which n is 1, X is a nitrogen atom and Y is CH or a $R_4$- or $R_5$-substituted carbon atom.

A sixth group of preferred compounds of formula (I) is one in which n is 1, X is CH or a $R_4$- or $R_5$-substituted carbon atom and Y is a nitrogen atom.

Particularly preferred compounds of formula (I) are those in which $R_5$ is hydrogen and $R_4$ is a

group
wherein $R_8$ is a $C_1$–$C_6$ alkyl, $C_1$–$C_4$ alkoxy or —$NR_6R_7$ group, $R_6$ or $R_7$ being as defined above.

Most preferred compounds are those in which $R_8$ is a -$NR_6R_7$ group and Z is oxygen.

The compounds of formula (I) or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula (I) or its salt or solvate.

One preferred pharmaceutically acceptable form is the crystalline form, including such form in a pharmaceutical composition. In the case of salts and solvates the additional ionic and solvent moieties must also be non-toxic.

Examples of pharmaceutically acceptable salts of a compound of formula (I) include acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic acids.

Examples of pharmaceutically acceptable solvates of a compound of formula (I) include hydrates.

The compounds of formula (I) may exist as cis or trans isomers, and the invention extends to both such forms as well as to their single enantiomers and to mixtures thereof, including racemates.

The invention also provides processes for the preparation of the compounds of formula (I).

Compounds of formula (I) in which n is zero, X is NH and Y is a $R_5$-substituted carbon atom, are obtained by cyclization of ketones of formula (II) (J. Org. Chem. 54, 1442 (1989)) with hydrazones of formula (III), working in the presence of metal zinc in acetic buffer, analogously to the method described in *Khimiya Geterot. Soed.* 342–4, 1972; see scheme 1:

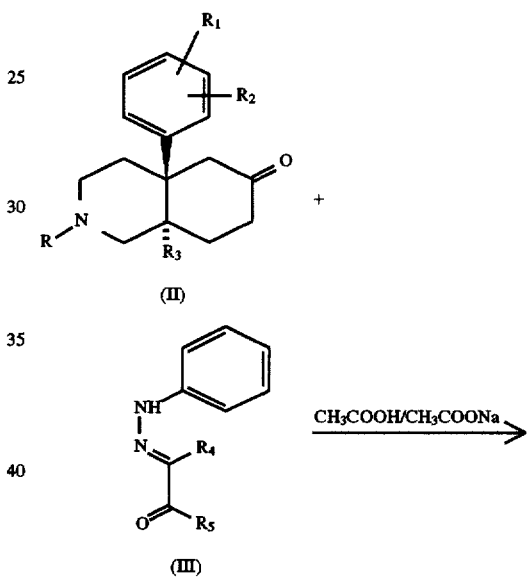

Compounds of formula (I) in which n is zero, X is NH and Y is a $R_4$-substituted carbon atom, are obtained by cyclization of bromoketones of formula (IV) (which may be obtained from ketones (II) by reaction with cupric bromide in chloroform, analogously to the method described in *J. Org. Chem.* 29,3459 (1964)), with ketones (V) in the presence of ammonia, analogously to the method described in *Can. J. Chem.* 48,1689 (1970); see scheme 2:

Scheme 2

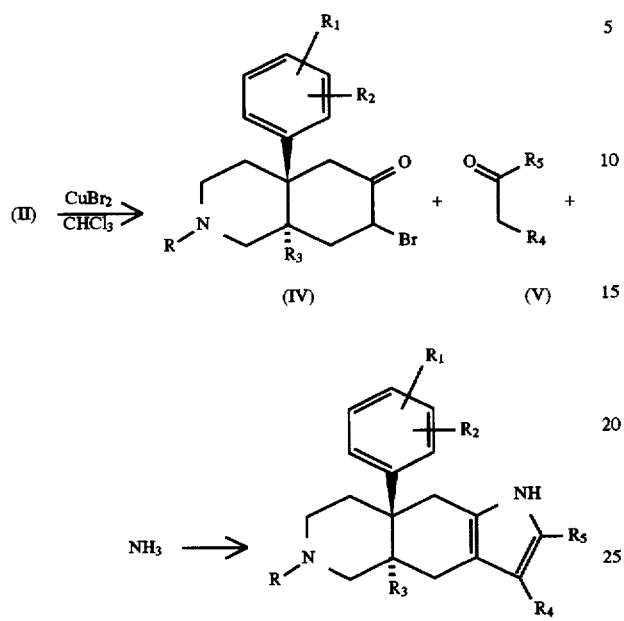

Compounds of formula (I) in which n is zero, X is oxygen and Y is a $R_5$-substituted carbon atom, are obtained by cyclization of ketones (II) with α-haloketones (preferably α-chloroketones) (VI), in the presence of bases, analogously to the method described in *J. Org. Chem.* 49,2317 (1984); see scheme 3:

Scheme 3

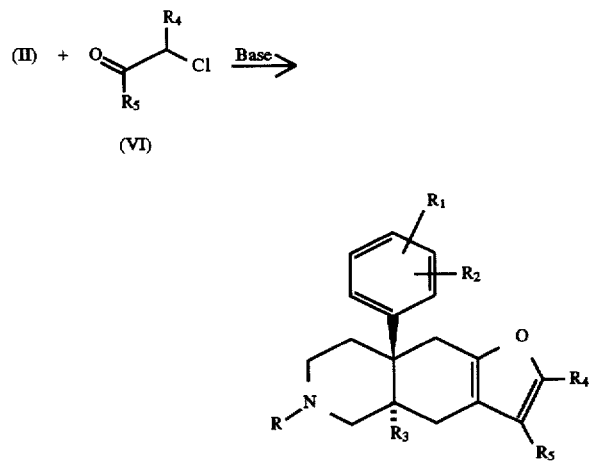

Compounds of formula (I) in which n is zero, X is oxygen and Y is a $R_4$-substituted carbon atom, are obtained by cyclization of bromoketones (IV) with ketones (V) in ethanol, in the presence of a base (suitably sodium ethoxide) analogously to the method described in *J. Chem. Soc. Perkin* I, 2372, (1972); see sceme 4

Scheme 4

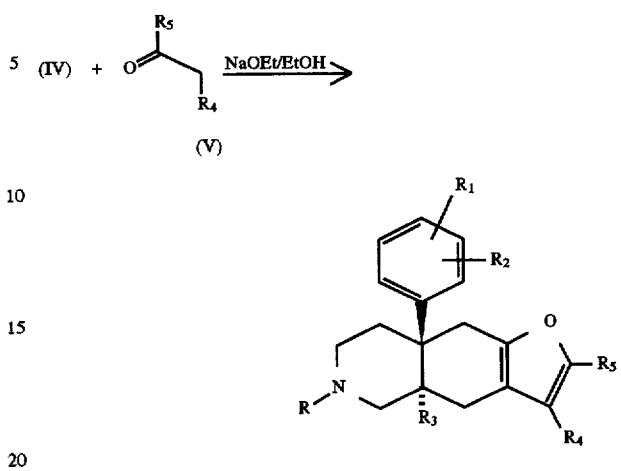

Compounds of formula (I) in which n is zero, X is sulphur and Y is a $R_5$ substituted carbon atom, are obtained by reacting β-diketones (VII) (which can be prepared by Claisen condensation from ketones (II) and esters of formula $R_5$-COOEt; *J. Am. Chem. Soc*, 67, 1510, 1945) with mercaptans (VIII) in the presence of hydrochloric acid, analogously to the method described in DE 1.088.507 (C.A. 56,457 (1962)); see scheme 5:

Scheme 5

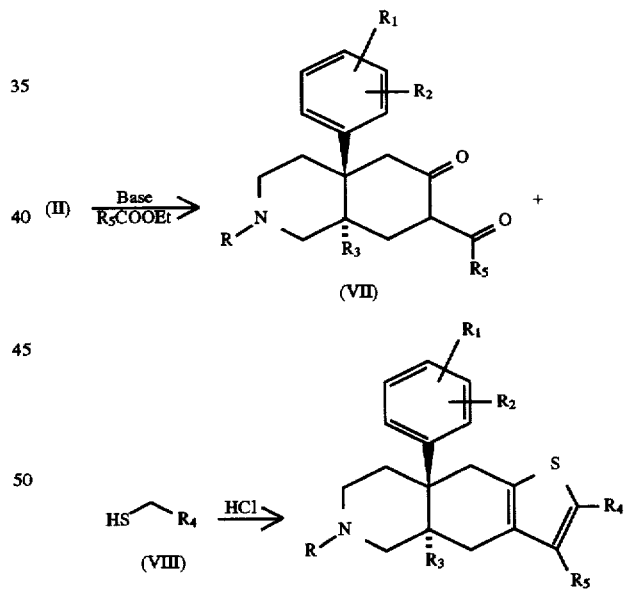

Compounds of formula (I) in which n is zero, Y is sulphur and X is a $R_4$-substituted carbon atom are obtained by reacting α-mercaptoketones (IX) (which are prepared starting from bromoketones (IV) and $H_2S$ in potassium hydroxide (*J. Am. Chem. Soc.* 197, 4175 (1985)) with acetylene derivatives (X), in aprotic solvents (preferably dimethylsulfoxide) in the presence of bases such as potassium tertbutoxide, as described in *Chem. Ber.* 97, 2109 (1964); see scheme 6:

Scheme 6

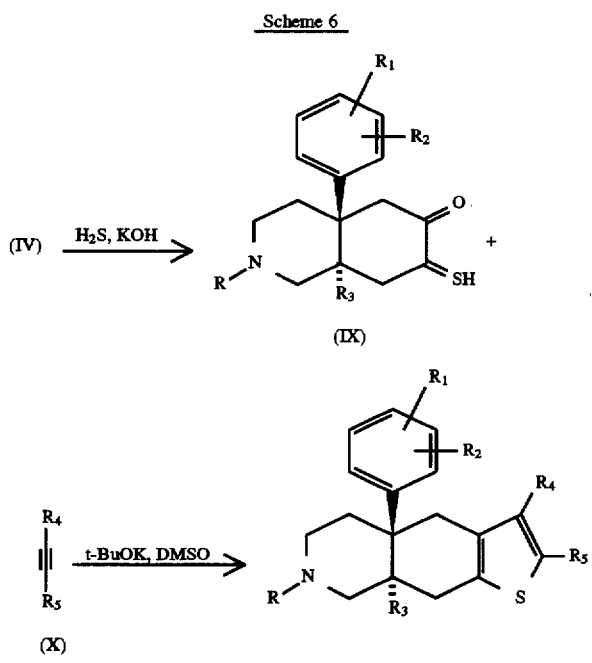

Compounds of formula (I) in which n is 1, X is a nitrogen atom and Y is CH are obtained by reacting hydroxymethyleneketones (XI) (which can be prepared from ketones (II) by condensation with ethyl formate in the presence of a base; *Org. Synth. Coll.* Vol. 4, 536, 1963) with enamine (XII), analogously to the method described in *J. Ind. Chem. Soc,* 12, 289 (1935); see scheme 7:

Scheme 7

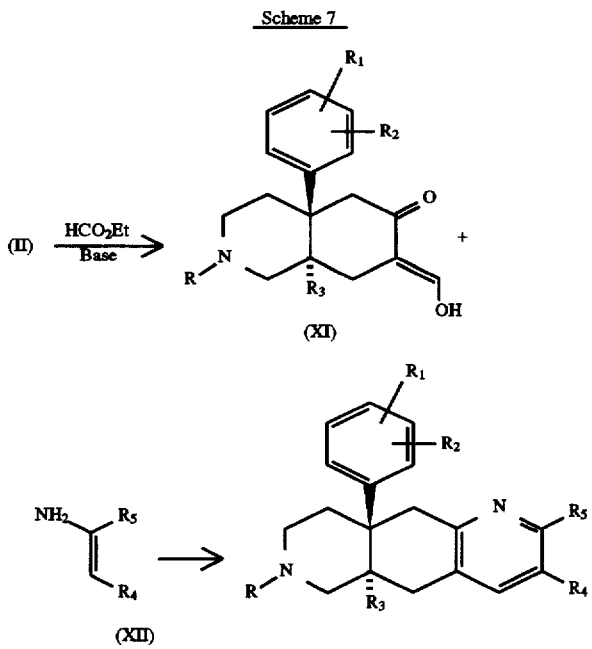

Compounds of formula (I) in which n is 1 and both X and Y are nitrogen atoms are obtained according to the invention by reacting of α-hydroxyiminoketones (XIII) (which can be prepared by reacting ketones (II) with isoamyl nitrite and potassium tert-butoxide; *J. Met. Chem.* 34, 1715, 1991) with ethanediamine (XIV) and subsequent aromatization of the intermediate by oxidation in basic medium, analogously to the method described in *Chem. Ber.* 100, 555 (1967); see scheme 8:

Scheme 8

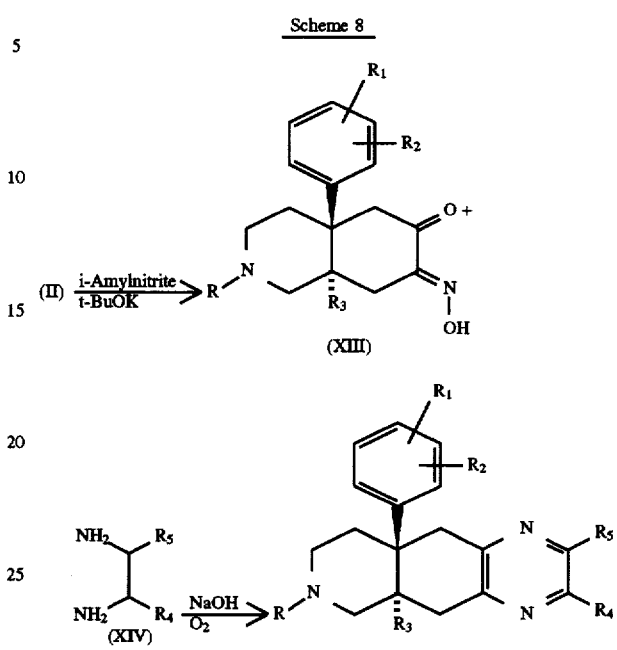

Compounds of formula (I) in which n=0, X and Y are both N, may be obtained from hydroxyimino derivatives (XV) and $R_4$-$R_5$-substituted chloroimidates of formula (XVI) in basic media, and subsequent treatment of the intermediates with $H^+$ in refluxing toluene (*J. Org. Chem.*, 58, 7092, (1993)) as described in scheme 9:

Scheme 9

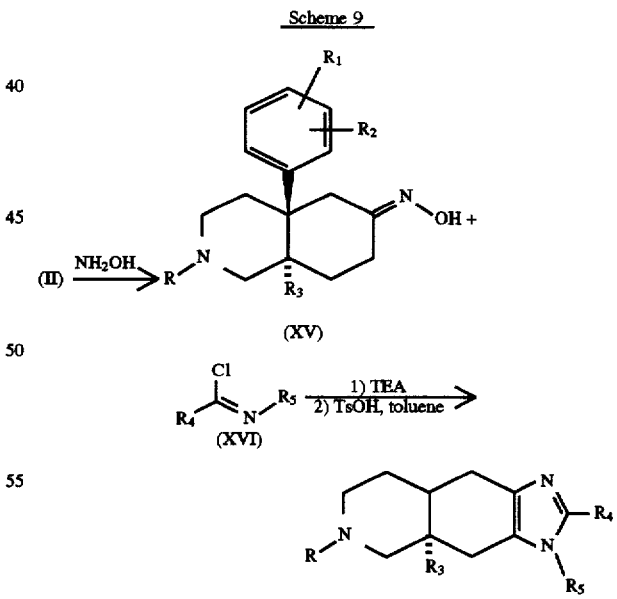

The compounds of formula (I) in which n is zero, Y is an heteroatom and X is a $R_4$- or $R_5$-substituted carbon atom (or in which n is 1, X and Y are both nitrogen atoms and the substituents $R_5$ and $R_4$ are reversed) can be obtained according to analogous schemes to those shown above, starting from isomer ketones of formula (IIa)

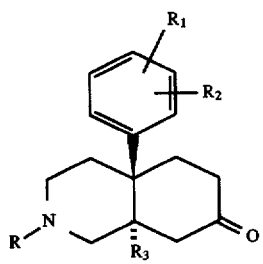

(IIa)

which can in their turn be obtained according to the method described in *J. Med. Chem.* 35, 48 (1992).

The processes of the invention also comprise the conversions of substituent groups into other substituent groups, carried out according to per se known methods, on the final compounds (I): for example demethylation of methoxy groups to hydroxy groups, or alkylation of the latter or of SH or NH groups, and the like.

As mentioned before, the compounds of formula (I) exist in more than one stereoisomeric form and the process of the invention produces mixtures thereof.

The individual isomers may be obtained from the enantiomerically pure intermediates.

The individual forms of the compounds of formula (I) may be separated one from another by resolution using an optically active acid such as tartaric acid or O,O'-di-p-toluoyltartaric acid. Alternatively, the single enantiomers can be prepared by an asymmetric synthesis.

The compounds of formula (I) may be converted into their pharmaceutically acceptable acid addition salts by reaction with the appropriate organic or mineral acids.

Solvates of the compounds of formula (I) may be formed by crystallisation or recrystallisation from the appropriate solvent. For example hydrates may be formed by crystallisation or recrystallisation from aqueous solutions or solutions in organic solvents containing water.

The salts or the solvates of the compounds of formula (I) which are not pharmaceutically acceptable can also be useful as intermediates in the preparation of pharmaceutically acceptable salts or solvates. Therefore, said salts or solvates are also part of this invention.

The activity of compounds of formula (I) in standard tests shows they are of potential therapeutic utility in the treatment of pain, in the prevention of rejection in organ transplants and skin grafts and, generally, for the treatment of pathological conditions which can be treated or alleviated by opioid δ receptor agonists or antagonists.

Accordingly the present invention also provides a compound of formula (I), or a pharmaceutically acceptable salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of pain, for the prevention of the rejection of organ transplants and skin grafts and, generally, for the treatment of pathological conditions which can be treated or alleviated by opioid δ receptor agonists or antagonists. Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents.

Preferably, a pharmaceutical composition of the invention is in unit dosage form and in a form suitable for use in the medical or veterinarian fields. For example, such preparations may be in a pack form accompanied by written or printed instructions for use as an agent in the treatment of pain, as an immunomodulating and/or immunosuppressive agent and, generally, as opioid δ receptor agonists or antagonists agents.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinyl-pyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Liquid compositions for oral administration may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by non-oral route. In accordance with routine pharmaceutical procedure, the compositions may be formulated, for example for rectal administration as a suppository. They may also be formulated, for presentation in an injectable form, in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to make the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn, or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day, for example 2, 3 or 4 times daily, and the total daily dose for a 70 kg adult will normally be in the range 100 to 3000 mg. Alternatively the unit dose will contain from 2 to 20 mg of active ingredient and be administered in multiple doses, if desired, to give the above mentioned daily dose.

No unacceptable toxicological effects are expected with compounds of the invention when administered in accordance with the invention.

The present invention also provides a method for the treatment and/or prophylaxis of pain and of rejection of transplants and skin grafts in mammals, particularly humans, which comprises administering to the mammal in need of such treatment and/or prophylaxis an effective amount of a compound of formula (I) or a pharmaceutically acceptable salt or solvate thereof.

Compounds of this invention and their preparation are illustrated in the following Examples, the preparation of intermediates being illustrated in the Preparations.

PREPARATION 1

N,N Diethyl-3-oxobutyramide 40 g (0.31 mol) of ethyl acetoacetate and 24 g (0.33 mol) of diethylamine were stirred in a Parr apparatus at 150° C. for 10'. The crude mixture was distilled at 115°–120° C./9 mmHg, to give 32 g of the title compound.

$C_8H_{15}NO_2$ IR (neat): 2980, 1725, 1640, 1590 $cm^{-1}$. N.M.R. 80 MHz (CDCl$_3$): δ3.6–3.1 (m, 6H); 2.2 (s, 3H), 1.1 (dt, 6H).

PREPARATION 2

N,N-Diethyl-2-phenylhydrazono-3-oxobutyramide 15.7 g (0.1 mol) of N,N-diethyl-3-oxobutyramide were mixed with 12 g (0.14 mol) of CH$_3$COONa, 20 ml of water and 75 ml of ethanol. The solution obtained was cooled to 10° C. and 0.1 mol of freshly prepared solution of phenyldiazonium chloride [Organic Reactions, R. Adams Ed; Wiley, New York, 10, 32–33, (1951–1959)] were added dropwise. The precipitated solid was filtered, dried in vacuo yielding 22.6 g of the title compound. M.p.=63°–65° C.

$C_{14}H_{19}N_3O_2$ IR (neat): 2970, 1720, 1620, 1605, 1560, 1245 $cm^{-1}$. N.M.R. 300 MHz (CDCl$_3$): δ9.3 (s, 1H); 7.4–7.2 (m, 5H); 3.6 (q, 2H); 3.2 (q, 2H ); 2.5 (s, 3H); 1.35 (t, 3H); 1.2 (t,3H). MS (TSP) m/z=262.1 (MH$^+$)

PREPARATION 3

N,N-Dipropyl-3-oxobutyramide 43.4 g (43.3 mol) of ethyl acetoacetate and 33.7 g (43.3 mol) of dipropylamine were treated as described in preparation 1. The crude oil was distilled at 86°–89° C./ 0.8 mmHg, to give 44.3 g of the title compound.

$C_{10}H_{19}NO_2$ I.R. (neat): 2980, 1725, 1640, 1590 $cm^{-1}$. N.M.R. 80 MHz (CDCl$_3$): δ3.45 (s, 2H), 3.4–2.9 (m, 4H), 2.3 (s, 3H), 1.7–1.2 (m 4H), 0.9–0.6 (t, 6H). MS (TSP) m/z=186.3 (MH$^+$)

PREPARATION 4

N,N -Dipropyl-2-phenylhydrazono-3-oxobutyramide 18.5 g (0.1 mol) of N,N-dipropyl-3-oxobutyramide, 12 g (0.146 mol) of CH$_3$COONa, 20 ml of water, 75 ml of ethanol and a solution of 0.1 mol of phenyldiazonium chloride were treated as described in preparation 2. The precipitated solid was filtered and dried in vacuo yielding 4.2 g of the title compound. M.p.=79°–80° C.

$C_{16}H_{23}N_3O_2$ I.R. (KBr): 2970, 1670, 1610, 1495 $cm^{-1}$ N.M.R. 300 MHz (CDCl$_3$): δ7.3 (s, 1H), 7.4–7.0 (m, 5H), 3.5–3.1 (st, 4H), 2.5 (s, 3H), 1.75–1.5 (m, 4H), 1.0 (t, 3H), 0.75 (t, 3H). MS (TSP) m/z=290.4 (MH$^+$)

PREPARATION 5 i-Butyl acetoacetate 30 ml of ethyl acetoacetate were dissolved in 350 ml of i-butyl alcohol and a catalytic amount of p-toluensulphonic acid (PTSA) was added. The solution was refluxed for 18 h. The reaction mixture was evaporated in vacuo and the residue was dissolved in ether. The resulted solution was treated with s.s. NaHCO$_3$. The organic layer was separated, dried over Na$_2$SO$_4$ and evaporated in vacuo. The crude oil was distilled at 66°–68° C./4 mmHg, to give 18.8 g of the title compound.

$C_8H_{14}O_3$ MS (TSP) m/z=159.3 (MH$^+$)

PREPARATION 6 i-Butyl 2-phenylhydrazono-3-oxobutyrate 15.8 g (0.1 mol) of i-butyl acetoacetate, 12 g (0.146 mol) of CH$_3$COONa, 20 ml of water, 75 ml of ethanol and a solution of 0.1 mol of phenyldiazonium chloride were treated as described in preparation 2. The precipitated solid was filtered an dried in vacuo yielding 23.1 g of the title compound. M.p.=45°–50° C.

$C_{14}H_{18}N_2O_3$ I.R. (KBr): 2970, 1690, 1600, 1530 $cm^{-1}$ N.M.R. 300 MHz (CDCl$_3$): δ10–9.2 (bs, 1H), 7.4–7.1 (m, 5H), 4.1 (d, 4H), 2.5 (s, 3H), 1.75–1.5 (m, 4H), 1.0 t, 3H), 0.75 (t, 3H). MS (TSP) m/z=263.3 (MH$^+$)

PREPARATION 7

N-Benzyl-3-oxobutyramide 9 ml (0.05 mol) of 2,2,6-trimethyl-4H-1,3-dioxin-4-one (diketene-acetone adduct) were added dropwise to a solution of 5.5 ml (0.05 mol) of benzylamine in 20 ml of toluene and the temperature was allowed to rise 70° C. The solution was refluxed for 2 h then the solvent was removed in vacuo. The crude product was triturated with ether obtaining 7.5 g of the title compound. M.p.=84°–86° C.

$C_{11}H_{13}NO_2$ I.R. (KBr): 3250, 3080, 1720, 1645 cm$^{-1}$

PREPARATION 8

N-Benzyl-2-phenylhydrazono-3-oxobutyramide 7.27 g (0.038) of N-benzyl-3-oxobutyramide were dissolved in a solution of 5.32 g (0.133 mol) of NaOH in 58 ml of water. To the ice-cooled stirred solution, 0.040 mol of phenyldiazonium chloride were added dropwise at such a rate as to keep the temperature at 0° C. The precipitated solid was filtered and recrystallised from MeOH yielding 9 g of the title compound. M.p.=101°–103° C.

$C_{17}H_{17}N_3O_2$ I.R. (KBr): 3300, 1650, 1510, 1245 cm$^{-1}$

PREPARATION 9

1-(3-Oxobutyryl)pyrrolidine 9 ml (0.05 mol) of diketene-acetone adduct and a solution of 4.2 ml (0.05 mol) of pyrrolidine in 20 ml of toluene were treated as described in preparation 7. The solvent was removed in vacuo and the residue was purified by chromatography on silica gel (EtOAc/MeOH 0%→1%) yielding 7.6 g of the title compound as a dark oil.

$C_8H_{13}NO_2$ I.R. (neat): 2980, 2880, 1725, 1645 cm$^{-1}$ MS (TSP) m/z=156 (MH$^+$)

PREPARATION 10

1-2-Phenylhydrazono-3-oxobutyryl)pyrrolidine 7.6 g (0.049 mol) of 1-(3-oxobutyryl)pyrrolidine, a solution of 6.86 g (0.17 mol) of NaOH in 75 ml of water and 0.051 mol of phenyldiazonium chloride were treated as described in preparation 8. The crude reaction mixture was purified by chromatography on silica gel (Et$_2$O) obtaining 8 g of the title compound which was used as such in the subsequent step.

PREPARATION 11

N-Phenyl-2-phenylhydrazono-3-oxobutyramide 4.5 g (25.4 mmol) of acetoacetanilide, a solution of 3.46 g (89 mmol) of NaOH in 45 ml of water and 95 mmol of phenyldiazonium chloride were treated as described in preparation 8. The residue was crystallised from EtOH, yielding 3.4 g of the title compound. M.p.=96°–97° C.

$C_{16}H_{15}N_3O_2$ I.R. (KBr): 3080, 1675, 1600, 1520 cm$^{-1}$ MS (TSP) m/z=282.2 (MH$^+$)

PREPARATION 12

N,N-Dimethyl-3-oxobutyramide

A solution of 9 ml (0.05 mmol) of diketene-acetone adduct in 20 ml of toluene was treated with gaseous dimethylamine at room temperature until the reaction was complete. The solvent was removed in vacuo and the residue was purified by chromatography on silica gel (EtOAc/MeOH 0%→10%) yielding 7.0 g of the title compound.

$C_6H_{11}NO_2$ I.R. (neat): 2940, 1720, 1640 cm$^{-1}$

PREPARATION 13

N,N-Dimethyl-2-phenylhydrazono-3-oxobutyramide 4.5 g (0.035 mol) of N,N-dimethyl-3-oxobutyramide, a solution of 4.9 g (0.122 mol) of NaOH in 45 ml of water and 0.037 mol of phenyldiazonium chloride were treated as described in preparation 8. The crude reaction mixture was purified by chromatography on silica gel (hexane/Et$_2$O 0%→100%) obtaining 3.5 g of the title compound which was used as such in the subsequent step. M.p.=131°–133° C.

$C_{12}H_{15}N_3O_2$ I.R. (KBr): 3205, 1720, 1630, 1565 cm–1

PREPARATION 14

3-Oxobutyramide

A solution of 9 ml (0.05 mmol) of diketene-acetone adduct in 20 ml of toluene was treated with gaseous ammonia as described in preparation 12. The solvent was removed in vacuo and the residue was purified by chromatography on silica gel (EtOAc) yielding 5.0 g of the title compound.

$C_4H_7NO_2$ I.R. (neat): 3300, 1730, 1640 cm$^{-1}$

PREPARATION 15

2-Phenylhydrazono-3-oxobutyramide 5.0 g (0.049 mol) of 3-oxobutyramide, a solution of 6.9 g (0.171 mol) of NaOH in 75 ml of water and 0.051 mol of phenyldiazonium chloride were treated as described in preparation 8. The crude reaction mixture was purified by chromatography on silica gel(EtOAc) obtaining 3 g of the title compound which was used as such in the subsequent step. M.p.=146°–147° C.

$C_{10}H_{11}N_3O_2$ I.R. (KBr): 3320, 1720, 1520 cm$^{-1}$

PREPARATION 16

N,N-Diisopropyl-3-oxobutyramide 9 ml (0.05 mol) of diketone-acetone adduct and a solution of 47.0 ml (0.05 mol) of diisopropylamine in 20 ml of toluene were treated as described in preparation 7. The solvent was removed in vacuo and the residue was purified by chromatography on silica gel (Et$_2$O) yielding 7.0 g of the title compound as a dark oil.

$C_{10}H_{19}NO_2$ I.R. (neat): 2980, 1725, 1640 cm$^{-1}$

PREPARATION 17

N,N-Diisopropyl-2-phenylhydrazono-3-oxobutyramide 7.0 g (0.038 mol) of N,N-diisopropyl-3-oxobutyramide, a solution of 5.3 g (0.133 mol) of NaOH in 58 ml of water and 0.04 mol of phenyldiazonium chloride were treated as described in preparation 8. The crude reaction mixture was purified by chromatography on silica gel (hexane/Et$_2$O 95:5) obtaining 7.5 g of the title compound which was used as such in the subsequent step. M.p.=143°–145° C.

$C_{16}H_{23}N_3O_2$ I.R. (KBr): 3210, 2980, 1650, 1620 cm$^{-1}$

PREPARATION 18

Ethyl 2-phenylhydrazono-4,4,4-trifluoro-3-oxobutyrate 7.3 ml (0.05 mol) of ethyl 3-oxo-4,4,4-trifluoroacetoacetate, 6 g (0.073 mol) of CH$_3$COONa, 20 ml of water, 37.5 ml of ethanol and a solution of 0.05 mol of phenyldiazonium chloride were treated as described in preparation 2. The crude product was purified by chromatography on silica gel (hexane/Et$_2$O 0%→25%) obtaining 8.65 g of the title compound. M.p.=78°–80° C.

$C_{12}H_{11}F_3N_2O_3$ I.R. (KBr): 1710, 1530 cm$^{-1}$ N.M.R. 300 MHz (DMSO-d$_6$): δ12.8 (s, 1H), 7.8–7.2 (m, 5H), 4.2 (q, 2H), 1.5 (t, 3H). MS (EI) m/z=288.0 (M$^+$).

PREPARATION 19

(±)-trans-4a-(3-Methoxyphenyl)-6-oxo-1,2,3,4,4a,5, 6,7,8,8a-decahydroisoquinoline hydrochloride A solution of 1.2 g (4.2 mmol) of (±)-trans-2-ethyl-4a-(3-methoxyphenyl)-6-oxo-1,2,3,4,4a,5,6,7,8,8a-decahydroisoquinoline and 1.8 g (12.6 mmol) of proton sponge in 34 ml of 1,2-dichloroethane was treated with 1.4 ml (16.8 mmol) of vinylchloroformate at 0° C. under nitrogen atmosphere. The reaction mixture was stirred at this temperature for 15 min and then refluxed for 3 h, the solvent was removed in vacuo, the residue was taken up in water and extracted with Et$_2$O. The organic layer was washed with 3% HCl, then was dried over Na$_2$SO$_4$ and the solvent was removed in vacuo. The dark residue was dissolved in EtOH, 3 ml of concentrated HCl were added and the solution refluxed for 3 hours. The solvent was removed in vacuo, obtaining 0.88 g of the title compound which was used as such in the subsequent step. M.p.=90° C. dec.

$C_{16}H_{21}NO_2 \cdot HCl$ I.R. (KBr): 3400, 2970, 1715, 1600 cm$^{-1}$

PREPARATION 20

(±)-trans-2-Cyclopropylmethyl-4a-(3-methoxyphenyl)-6-oxo-1,2,3,4,4a,5,6,7,8,8a-decahydroisoquinoline hydrochloride 0.88 g (3.08 mmol) of (±)-trans-4a-(3-methoxyphenyl)-6-oxo-1,2,3,4,4a,5,6,7,8,8a-decahydroisoquinoline hydrochloride, 0.44 g (3.23 mmol) of cyclopropylmethyl bromide, 0.64 g of potassium carbonate and a catalytical amount of potassium iodide in 15.4 ml of DMF were stirred at 60° C. for 2 h. The solvent was removed in vacuo, and the crude product was purified by flash chromatography (EtOAc/MeOH/conc. NH$_4$OH 90:10:0.8). The solid product was dissolved in acetone and the solution brought to acidic pH with HCl/Et$_2$O. The precipitate was filtered, yielding 0.28 g of the title compound. M.p.=78° C. dec.

$C_{20}H_{27}NO_2 \cdot HCl$ I.R. (KBr): 3400, 2940, 1715, 1600 cm$^{-1}$ N.M.R. 300 MHz (DMSO-d$_6$): δ7.4–6.8 (m, 4H), 3.8 (s, 3H), 3.6–1.1 (m, 16H), (m, 2H), 0.4 (m, 2H). MS (EI) m/z=314.2 (MH$^+$).

PREPARATION 21

(±)-trans-2-Diethylaminocarbonyl-8a-(3-methoxyphenyl)-3-methyl-4,4a,5,6,7,8, 8a-octahydro-1H-pyrrolo[2,3-g]isoquinoline hydrochloride A solution of 0.6 g (1.42 mmol) of (±)-trans-2-diethylaminocarbonyl-6-ethyl-8a-(3-methoxyphenyl)-3-methyl-4,4a,5,6,7,8,8a-octahydro-1H-pyrrolo[2,3-g] isoquinoline hydrochloride and 0.6 g (2.48 mmol) of proton sponge in 35 ml of 1,2-dichloroethane was treated with 0.245 ml (2.48 mmol) of vinylchloroformate and then with conc. HCl in EtOH as described in preparation 19, obtaining 0.36 g of the title compound.

$C_{24}H_{33}N_3O_2 \cdot HCl$ I.R. (KBr): 3400, 2970, 1755, 1600 cm$^{-1}$

PREPARATION 22

(±)-trans-2-Butyl-4a-(3-methoxyphenyl)-6-oxo-1,2, 3,4,4a,5,6,7,8, 8a-decahydroisoquinoline 0.71 g (2.55 mmol) of (±)-trans-4a-(3-methoxyphenyl)-6-oxo-1,2,3,4,4a,5,6,7,8, 8a-decahydroisoquinoline hydrochloride, 0.37 g (2.68 mmol) of butyl bromide, 0.53 g of potassium carbonate and a catalytical amount of potassium iodide in 15 ml of DMF were reacted as described in preparation 20, yielding 0.2 g of the title compound which was used as such in the subsequent step.

$C_{20}H_{29}NO_2$ I.R. (neat): 3400, 2930, 1715, 1605 cm$^{-1}$

PREPARATION 23

(±)-trans-2-Ethyl-6-hydroxyimino-4a-(3-methoxyphenyl)-1,2,3,4,4a,5,6,7,8, 8a-decahydroisoquinoline 0.5 g (1.54 mmol) of (±)-trans-2-ethyl-4a-(3-methoxyphenyl)-6-oxo-1,2,3,4,4a,5,6,7,8,8a-decahydroisoquinoline hydrochloride, 0.456 g (6.56 mmol) of hydroxylamine hydrochloride and 0.64 g of KHCO$_3$ in 10 ml of MeOH were refluxed for 45 min. The precipitate was filtered, the solvent was removed in vacuo and the residue taken up in H$_2$O. The pH was adjusted to 8 with conc. NH$_4$OH, the aqueous layer was extracted with CH$_2$Cl$_2$. The organic layer was dried, the solvent removed in vacuo, obtaining 0.45 g of the title compound which was used as such in the subsequent step.

$C_{18}H_{26}N_2O_2$ I.R. (KBr): 2940, 2820, 1605, 1580 cm$^{-1}$

PREPARATION 24

(±)-trans-2-Diisopropylaminocarbonyl-8a-(3-methoxyphenyl)-3-methyl-4,4a,5,6,7,8,8a-octahydro-1H-pyrrolo[2,3-g]isoquinoline hydrochloride A solution of 0.57 g (1.26 mmol) of (±)-trans-2-diisopropylaminocarbonyl-6-ethyl-8a-(3-methoxyphenyl)-3-methyl-4,4a,5,6,7,8,8a-octahydro-1H-pyrrolo [2,3-g] isoquinoline and 0.54 g (4.52 mmol) of proton sponge in 35 ml of 1,2-dichloroethane was treated with 0.77 ml (4.52 mmol) of vinyl chloroformate and then with conc. HCl in EtOH as described in preparation 19, obtaining 0.34 g of the title compound.

$C_{26}H_{37}N_3O_2 \cdot HCl$ I.R. (KBr): 3400, 2970, 1755, 1600 cm$^{-1}$

EXAMPLE 1

(±)-trans-2-Diethylaminocarbonyl-6-ethyl-8a-(3-methoxyphenyl)-3-methyl-4,4a,5,6,7,8,8a-octahydro-1H-pyrrolo[2,3-g]isoquinoline 1.6 g (4.9 mmol) of (±)-trans-2-ethyl-4a-(3-methoxyphenyl)-6-oxo-1,2,3,4,4a,5,6,7,8,8a-decahydroisoquinoline hydrochloride (J. Med. Chem., 54, 1442, 1989) and 1.54 g (5.8 mmol) of N,N-diethyl-2-phenylhydrazono-3-oxobutyramide were dissolved in a mixture of 5 ml of glacial acetic acid and 0.48 g (5.8 mmol) of CH$_3$COONa. The solution was heated to 60° C. then, under N$_2$ atmosphere, 1.47 g (22.5 mmol) of zinc dust were added portionwise. The resulting mixture was refluxed for 2 h and cooled to room temperature. The precipitate was removed by decantation and washed with 5 ml of glacial acetic acid. The combined acidic solutions were diluted with iced water (50 ml), the pH was adjusted to 8 with 20% NaOH and then extracted with AcOEt. The organic layer was dried over Na$_2$SO$_4$ and the solvent was removed in vacuo. The residue was purified by flash chromatography (AcOEt/MeOH/conc. NH$_4$OH 90:10:1; Rf=0.25), yielding 1.4 g of the title compound. M.p. (HCl salt)=247° C. dec.

$C_{26}H_{37}N_3O_2$ I.R. (KBr) (·HCl): 3410, 3200, 2920, 2500, 1600, 1580 cm$^{-1}$. N.M.R. 80 MHz (CDCl$_3$): δ7.3 (s, 1H), 7.2–6.6 (m, 4H), 3.7 (s, 3H), 3.6–2.0 (m, 20H), 1.95 (s, 3H), 1.2–0.9 (m, 6H). MS (TSP) m/z=424.2 (MH⁺)

EXAMPLE 2

(±)-trans-2-Diethylaminocarbonyl-6-ethyl-8a-(3-hydroxyphenyl)-3-methyl-4,4a,5,6,7,8,8a,9-octahydro-1H-pyrrolo[2,3-g]isoquinoline To a solution of 1.89 ml (20.2 mmol) of boron tribromide in 40 ml of dry $CHCl_3$, 1.43 g (3.37 mmol) of (±)-trans-2-diethylaminocarbonyl-6-ethyl-8a-(3-methoxyphenyl)-3-methyl-4,4a,5,6,7,8,8a,9-octahydro-1H-pyrrolo[2,3g]isoquinoline dissolved in 15 ml of dry $CHCl_3$ were added, under $N_2$ atmosphere, at room temperature. After 2 h the mixture was poured in 200 g of ice containing 20 ml of conc. $NH_4OH$. The organic layer was separated, dried over $Na_2SO_4$ and the solvent removed in vacuo. The residue was purified by flash chromatography (AcOEt/MeOH/conc. $NH_4OH$ 80:20:2), obtaining 0.8 g of the title compound. M.p.=221°–223° C.

$C_{25}H_{35}N_3O_2$ I.R. (KBr): 3500, 2940, 1575, 1300 cm⁻¹. N.M.R. 300 MHz (DMSO-d6): δ10.25 (s, 1H), 8.55 (s, 1H), 7.0–6.8 (m, 3H), 6.45 (d, 1H), 2.85–1.85 (m, 20H), 1.95 (s, 3H), 1.0 (dt, 6H). MS (TSP) m/z=410.2 (MH⁺)

EXAMPLE 3

(±)-trans-6-Ethyl-2-ethoxycarbonyl-3-methyl-8a-(3-methoxyphenyl)-4,4a,5,6,7,8,8a,9-octahydro-1H-pyrrolo[2,3-g]isoquinoline 0.8 g (2.47 mmol) of (±)-trans-2-ethyl-4a-(3-methoxyphenyl)-6-oxo-1,2,3,4,4a,5,6,7,8,8a-decahydroisoquinoline hydrochloride and 0.87 g (93.7 mmol) of ethyl 2-phenylhydrazono-3-oxobutyrate [Organic Reactions, R. Adams Ed; Wiley, New York, 10, 32–33, (1951–1959)] were dissolved in a mixture of 3 mi of glacial acetic acid and 0.34 g (4.2 mmol) of $CH_3COONa$. The solution was treated as described in example 1 adding 0.74 g (11.3 mmol) of zinc dust. The residue was purified by flash chromatography (AcOEt/MeOH/conc. $NH_4OH$ 94:5:0.5; Rf=0.3), obtaining 0.6 g of the title compound.

$C_{24}H_{32}N_2O_3$ I.R. (KBr): 3300, 2915, 1680, 1600, 1445 cm⁻¹ N.M.R. 300 MHz (DMSO-d6): δ10.8 (s, 1H), 7.2–6.6 (m, 4H), 4.1 (q, 2H), 3.65 (s, 3H), 3.1–2.2 (m, 11H), 2.1 (s, 3H), 1.7 (d, 2H), 1.1(t, 3H), 0.95 (t, 3H). MS (TSP) m/z=397.2 (MH⁺)

EXAMPLE 4

(±)-trans-6-Ethyl-2-ethoxycarbonyl-8a-(3-hydroxyphenyl)-3-methyl-4,4a,5,6,7,8,8a,9-octahydro-1H-pyrrolo[2,3-g]isoquinoline 0.6 g (1.5 mmol) of (±)-trans-6-ethyl-2-ethoxycarbonyl-3-methyl-8a-(3-methoxyphenyl)-4,4a,5,6,7,8,8a,9-octahydro-1H-pyrrolo[2,3-g]isoquinoline were treated with 0.84 ml (9.0 mmol) of boron tribromide as described in example 2. The crude solid was purified by flash chromatography (AcOEt/MeOH/conc. $NH_4OH$ 80:20:2), yielding 0.12 g of the title compound. M.p.=195°–197° C.

$C_{23}H_{30}N_2O_3$ I.R. (KBr): 3300, 2920, 1690, 1440 cm⁻¹. N.M.R. 300 MHz (DMSO-d6): δ10.8 (s, 1H), 9.1 (s, 1H), 7.1–6.4 (m, 3H), 4.1 (q, 2H), 3.45–1.75 (m, 14H), 2.1 (s, 3H), 1.2 (t, 3H), 1.0 (t, 3H). MS (TSP) m/z=383.1 (MH⁺)

EXAMPLE 5

(±)-trans-Dipropylaminocarbonyl-6-ethyl-3-methyl-8a-(3-methoxyphenyl)-4,4a,5,6,7,8,8a,9-octahydro-1H-pyrrolo[2,3-g]isoquinoline hydrochloride 0.7 g (2.16 mmol) of (±)-trans-2-ethyl-4a-(3-methoxyphenyl)-6-oxo-1,2,3,4,4a,5,6,7,8,8a-decahydroisoquinoline hydrochloride, 0.62 g (2.16 mmol) of N,N-dipropyl-2-phenylhydrazono-3-oxobutyramide, 0.21 g (2.6 mmol) of $CH_3COONa$, 0.65 g (10 mmol) of zinc dust and 2.5 ml of glacial acetic acid were treated as described in example 1. The residue was purified by flash chromatography (AcOEt/MeOH/conc. $NH_4OH$ 90:10:1.5; Rf=0.3), dissolved in $Et_2O$ and the solution brought to acidic pH with $HCl/Et_2O$. The precipitate was filtered and recrystallised from a mixture of AcOEt/Acetone=9/1, yielding 0.65 g of the title compound.

M.p.=250° C. dec. $C_{28}H_{41}N_3O_2 \cdot HCl$ I.R. (KBr): 3400, 3210, 2970, 1600, 1580 cm₃₁ ₁ N.M.R. 300 MHz ($CDCl_3$): δ12 (bs, 1H), 8.5 (s, 1H), 7.4–6.6 (m, 4H), 3.8–2.5 (m, 17H), 2.0 (s, 3H), 1.8–1.3 (m, 10H), 0.9 (t, 6H). MS (TSP) m/z (free base)=452.7 (MH⁺)

EXAMPLE 6

(±)-trans-Dipropylaminocarbonyl-6-ethyl-8a-(3-hydroxyphenyl)-3-methyl-4,4a,5,6,7,8,8a,9-octahydro-1H-pyrrolo[2,3-g]isoquinoline 0.56 g (1.15 mmol) of (±)-trans-dipropylaminocarbonyl-6-ethyl-3-methyl-8a-(3-methoxyphenyl)-4,4a,5,6,7,8,8a,9-octahydro-1H-pyrrolo[2,3-g]isoquinoline hydrochloride were treated with 0.65 ml (7 mmol) of boron tribromide as described in example 2. The residue was purified by flash chromatography (AcOEt/MeOH/conc. $NH_4OH$ 75:25:2.5). The crude product was crystallised from acetone yielding 0.075 g of the title compound. M.p.=151°–153° C.

$C_{27}H_{39}N_3O_2$ I.R. (KBr): 3150, 2970, 1590, 1450cm⁻¹ N.M.R. 300 MHz (DMSO-d₆): δ10.2 (s, 1H), 9.1 (s, 1H), 7.2–6.4 (m, 4H), 3.5–1.8(m, 17H), 1.9 (s, 3H), 1.6–1.4 (m, 4H), 1.0 (t, 3H), 0.8 (t, 6H). MS (TSP) m/z=438.4 (MH⁺)

EXAMPLE 7

(±)-trans-2-(i-Butoxycarbonyl)-6-ethyl-3-methyl-8a-(3-methoxyphenyl)-4,4a,5,6,7,8,8a,9-octahydro-1H-pyrrolo[2,3-g]isoquinoline hydrochloride 0.7 g (2.16 mmol) of (±)-trans-2-ethyl-4a-(3-methoxyphenyl)-6-oxo-1,2,3,4,4a,5,6,7,8,8a-decahydroisoquinoline hydrochloride, 0.56 g (2.16 mmol) of i-butyl 2-phenylhydrazono-3-oxobutyrate, 0.21 g (2.6 mmol) of $CH_3COONa$, 0.65 g (10 mmol) of zinc dust and 2.5 ml of glacial acetic acid were treated as described in example 1. The residue was purified by flash chromatography (AcOEt/MeOH/conc. $NH_4OH$ 90:10:1.5; Rf=0.27). The purified free base was dissolved in AcOEt and the solution brought to acidic pH with $HCl/Et_2O$. The precipitate was filtered, washed and dried, to yield 0.56 g of the title compound. M.p.=230° C. dec.

$C_{26}H_{36}N_2O_3 \cdot HCl$ I.R. (KBr): 3400, 2970, 1670, 1600 cm⁻¹ N.M.R. 300 MHz ($CDCl_3$): δ9.7 (bs, 1H), 8.4 (s, 1H), 7.3–6.6 (m, 4H), 4.0 (d,2H)3.8 (s, 3H), 3.6–2.5 (m, 13H), 2.2 (s, 3H), 2.1–1.4 (m, 4H), 1.0 (d, 6H).

EXAMPLE 8

(±)-trans-2-(i-Butoxycarbonyl)-6-ethyl-8a-(3-hydroxyphenyl)-3-methyl-4,4a,5,6,7,8,8a,9-octahydro-1H-pyrrolo[2,3-g]isoquinoline hydrochloride 0.56 g of (±)-trans-2-(i-butoxycarbonyl)-6-ethyl-3-methyl-8a-(3-methoxyphenyl)-4,4a,5,6,7,8,8a,9-octahydro-1H-pyrrolo[2,3-g]isoquinoline hydrochloride were treated with 0.68 ml (7.26 mmol) of boron tribromide as described in example 2. The residue was purified by flash chromatography (AcOEt/MeOH/conc. NH$_4$OH 75:25:2.5) and then crystallised from AcOEt yielding 0.1 g of the title compound. M.p.=196°–198° C.

C$_{25}$H$_{34}$N$_2$O$_3$ I.R. (KBr): 2960, 1620, 1580, 1320 cm$^{-1}$ N.M.R. 300 MHz (DMSO-$_6$): δ9.2 (s, 1H), 8.5 (s, 1H), 7.0–6.2 (m, 4H), 3.8 (d, 2H), 3.0–1.8 (m, 14H), 2.1 (s, 3H), 1.1–0.9 (m, 9H). MS (TSP) m/z=411.4 (MH$^+$)

EXAMPLE 9

(±)-trans-2-Diethylaminocarbonyl-3,6-dimethyl-8a-(3-methoxyphenyl)-4,4a,5,6,7,8,8a,9-octahydro-1H-pyrrolo[2,3-g]isoquinoline 3 g (9.3 mmol) of (±)-trans-2-ethyl-4a-(3-methoxyphenyl)-6-oxo-1,2,3,4,4a,5,6,7,8,8a-decahydroisoquinoline hydrochloride, 2.92 g (11.2 mmol) of N,N-diethyl-2-phenylhydrazono-3-oxobutyramide, 0.92 g (11.2 mmol) of CH$_3$COONa, 2.8 g (42.8 mmol) of zinc dust and 9.3 ml of glacial acetic acid were treated as described in example 1. The residue was purified by flash chromatography (AcOEt/MeOH/conc. NH$_4$OH 90:10:1; Rf=0.27) yielding 0.56 g of the title compound. M.p. (.HCl)=250° C. dec.
C$_{25}$H$_{35}$N$_3$O$_2$ I.R. (KBr) (hydrochloride): 3410, 3200, 2915, 2510, 1605, 1580 cm$^{-1}$.

EXAMPLE 10

(±)-trans-2-Diethylaminocarbonyl-3,6-dimethyl-8a-(3-hydroxyphenyl)-4,4a,5,6,7,8,8a,9-octahydro-1H-pyrrolo[2,3-g]isoquinoline hydrochloride 0.5 g (1.22 mmol) of (±)-trans-2-diethylaminocarbonyl-3,6-dimethyl-8a-(3-methoxyphenyl)-4,4a,5,6,7,8,8a,9-octahydro-1H-pyrrolo[2,3-g]isoquinoline were treated with 0.68 ml (7.26 mmol) of boron tribromide as described in example 2. The residue was purified by flash chromatography (AcOEt/MeOH/conc. NH$_4$OH 75:25:2.5). The crude product was dissolved in MeOH and the solution brought to acidic pH with HCl/Et$_2$O. The solvent was evaporated in vacuo and the solid crystallised from a mixture of acetone/MeOH=1:1, yielding 0.06 g of the rifle compound.M.p.=>250° C.

C$_{24}$H$_{33}$N$_3$O$_2$.HCl I.R. (KBr): 3450, 3120, 2970, 1600, 1580 cm$^{-1}$ N.M.R. 300 MHz (DMSO-$_6$): δ10.4 (s, 1H), 9.2 (s, 1H), 7.2–6.5 (m, 4H), 3.5–2.0(m, 15H), 2.8 (s, 3H), 1.9 (s, 3H), 1.0 (t, 6H). MS (TSP) m/z(free base)=396.4 (MH$^+$)

EXAMPLE 11

(±)-trans-2-Diethylaminocarbonyl-3,7-dimethyl-4a-(3-methoxyphenyl) -4,4a,5,6,7,8,8a,9-octahydro-1H-pyrrolo[3,2-g]isoquinoline 0.9 g (2.9 mmol) of (±)-trans-2-ethyl-4a-(3-methoxyphenyl)-7-oxo-1,2,3,4,4a,5,6,7,8,8a-decahydroisoquinoline hydrochloride (J. Med. Chem., 35, 48, 1992), 0.9 g (3.5 mmol) of N,N-diethyl-2-phenylhydrazono-3-oxobutyramide, 0.28 g (3.5 mmol) of CH$_3$COONa, 0.87 g (13.3 mmol) of zinc dust and 5 ml of glacial acetic acid were treated as described in example 1. The residue was purified by flash chromatography (CH$_2$Cl$_2$/MeOH/conc. NH$_4$OH 86: 10:0.6; Rf=0.27), to yield 0.2 g of the title compound.M.p.=153°–155° C. dec.

C$_{25}$H$_{35}$N$_3$O$_2$ I.R. (KBr): 3250, 2920, 1605, 1580 cm$^{-1}$. N.M.R. 300 MHz (CDCl$_3$): δ8.2 (s, 1H), 7.1–6.6 (m, 4H), 3.7 (s, 3H), 3.6–1.59(m, 15H), 2.3 (s, 3H), 1.9 (s, 3H), 1.1 (t, 6H). MS (TSP) m/z=410.5 (MH$^+$)

EXAMPLE 12

(±)-trans-2-Diethylaminocarbonyl-3,7-dimethyl-4a-(3-hydroxyphenyl)-4,4a,5,6,7,8,8a,9-octahydro-1H-pyrrolo[3,2-g]isoquinoline 0.29 g (0.71 mmol) of (±)-trans-2-diethylaminocarbonyl-3,7-dimethyl-4a-(3-methoxyphenyl)-4,4a,5,6,7,8,8a,9-octahydro-1H-pyrrolo[3,2-g]isoquinoline were treated with 0.4 ml (4.26 mmol) of boron tribromide as described in example 2. The residue was purified by flash chromatography (CH$_2$Cl$_2$ /MeOH/conc. NH$_4$OH 80:12:0.8). The crude product was triturated with a mixture of acetone/MeOH= 3:2, yielding 0.14 g of the title compound. M.p.=235°–238 1° C.

C$_{24}$H$_{33}$N$_3$O$_2$ I.R. (KBr): 3215, 2920, 1610, 1510 cm$^{-1}$ N.M.R. 300 MHz (DMSO-$_6$): δ10.4 (s, 1H), 9.1 (s, 1H), 7.0–6.4 (m, 4H), 3.4–2.0(m, 15H), 2.2 (s, 3H), 1.9 (s, 3H), 1.0 (t, 6H). MS (TSP) m/z=396.4 (MH$^+$)

EXAMPLE 13

(±)-trans-2-Benzylaminocarbonyl-3,6-dimethyl-8a-(3-methoxyphenyl)-4,4a,5,6,7,8,8a,9-octahydro-1H-pyrrolo[2,3-g]isoquinoline 1 g (3.3 mmol) of (±)-trans-2-ethyl-4a-(3-methoxyphenyl)-6-oxo-1,2,3,4,4a,5,6,7,8,8a-decahydroisoquinoline hydrochloride, 2.95 g (10 mmol) of N-benzyl-2-phenylhydrazono-3-oxobutyramide, 0.82 g (10 mmol) of CH$_3$COONa, 2.6 g (40 mmol) of zinc dust and 5 ml of glacial acetic acid were treated as described in example 1. The residue was crystallised from AcOEt yielding 0.65 g of the title compound. M. p.=162°–164° C.

C$_{28}$H$_{33}$N$_3$O$_2$ I.R. (KBr): 3350, 3220, 2920, 1640, 1630, 1510 cm$^{-1}$.

EXAMPLE 14

(±)-trans-2-Benzylaminocarbonyl-3,6-dimethyl-8a-(3-hydroxyphenyl)-4,4a,5,6,7,8,8a,9-octahydro-1H-pyrrolo[2,3-g]isoquinoline hydrochloride 0.38 g of (±)-trans-2-benzylaminocarbonyl-3,6-dimethyl-8a-( 3-methoxyphenyl)-4,4a,5,6,7,8,8a,9-octahydro-1H-pyrrolo[2,3-g]isoquinoline were treated with 0.55 ml (5.7 mmol) of boron tribromide as described in example 2. The residue was dissolved in MeOH and the solution brought to acidic pH with HCl/Et$_2$O. The solvent was evaporated in vacuo and the solid crystallised from a mixture of acetone/MeOH=1:1, yielding 0.15 g of the title compound. M.p.= 297°–299° C. C$_{27}$H$_{31}$N$_3$O$_2$.HCl I.R. (KBr): 3290, 2910, 1650, 1540, 1320cm$^{-1}$

EXAMPLE 15

(±)-trans-3,6-Dimethyl-8a-(3-methoxyphenyl)-2-pyrrolidinocarbonyl-4,4a,5,6,7,8,8a,9-octahydro-1H-pyrrolo[2,3-g]isoquinoline 1 g (3.3 mmol) of (±)-trans-2-ethyl-4a-(3-methoxyphenyl)-6-oxo-1,2,3,4,4a,5,6,7,8,8a-decahydroisoquinoline hydrochloride, 2.6 g (10 mmol) of 1-(2-phenylhydrazono-3-oxobutyryl)pyrrolidine, 0.82 g (10 mmol) of CH$_3$COONa, 2.6 g (40 mmol) of zinc dust and 5 ml of glacial acetic acid were treated as described in example 1. The residue was purified by chromatography on silica gel (EtOAc/MeOH 0%→5%) then crystallised from a mixture of acetone/MeOH=1:1 yielding 0.65 g of the title compound. M.p.=171°–173° C.

$C_{25}H_{33}N_3O_2$ I.R. (KBr): 3280, 2940, 1610, 1580 cm$^{-1}$.

EXAMPLE 16

(±)-trans-3,6-Dimethyl-8a-(3-hydroxyphenyl)-2-pyrrolidinocarbonyl-4,4a,5,6,7,8,8a,9-octahydro-1H-pyrrolo[2,3-g]isoquinoline hydrochloride 0.38 g of (±)-trans-3,6-dimethyl-8a-(3-methoxyphenyl)-2-pyrrolidinocarbonyl-4,4a,5,6,7,8,8a,9-octahydro-1H-pyrrolo[2,3-g]isoquinoline were treated with 0.55 ml (5.7 mmol) of boron tribromide as described in example 2. The residue was triturated in Et$_2$O and the solution brought to acidic pH with HCl/Et$_2$O. The solvent was evaporated in vacuo and the solid crystallised from a mixture of acetone/MeOH=1:1, yielding 0.15 g of the title compound. M.p.=230–233 °C.

$C_{24}H_{31}N_3O_2$.HCl I.R. (KBr): 3400, 3140, 1600, 1580, 1510 cm$^{-1}$

EXAMPLE 17

(±)-trans-6-Ethyl-3-methyl-8a-(3-methoxyphenyl)-2-phenylaminocarbonyl-4,4a,5,6,7,8,8a,9-octahydro-1H-pyrrolo[2,3-g]isoquinoline 0.8 g (2.47 mmol) of (±)-trans-2-ethyl-4a-(3-methoxyphenyl)-6-oxo-1,2,3,4,4a,5,6,7,8,8a-decahydroisoquinoline hydrochloride, 0.7 g (2.47 mmol) of N-phenyl-2-phenylhydrazono-3-oxobutyramide, 0.24 g (3 mmol) of CH$_3$COONa, 0.74 g (11.3 mmol) of zinc dust and 2.5 ml of glacial acetic acid were treated as described in example 1. The residue was purified by flash chromatography (EtOAc/MeOH/conc. NH$_4$OH 90:10:1) yielding 0.28 g of the title compound. M.p.=178–180° C.

$C_{28}H_{33}N_3O_2$ I.R. (KBr): 3280, 2940, 1640, 1590 cm$^{-1}$. N.M.R. 300 MHz (CDCl$_3$): δ7.6–6.6 (m, 9H), 3.75 (s, 3H), 3.0–2.4 (m, 14H), 1.9(q, 2H), 1.1 (t, 3H). MS (TSP) m/z=444.5 (MH$^+$)

EXAMPLE 18

(±)-trans-6-Ethyl-8a-(3-hydroxyphenyl)-3-methyl-2-phenylaminocarbonyl-4,4a,5,6,7,8,8a,9-octahydro-1H-pyrrolo[2,3-g]isoquinoline 0.28 g of (±)-trans-6-ethyl-8a-(3-methoxyphenyl)-3-methyl-2-phenylaminocarbonyl-4,4a,5,6,7,8,8a,9-octahydro-1H-pyrrolo[2,3-g]isoquinoline were treated with 0.35 (1.9 mmol) of boron tribromide as described in example 2. The residue was purified by flash chromatography (EtOAc/MeOH/conc. NH$_4$OH 80:20:2) yielding 0.06 g of the title compound. M.p.=271°–272° C.

$C_{27}H_{31}N_3O_2$.HCl I.R. (KBr): 3310, 294, 1640, 1590 cm$^{-1}$ N.M.R. 300 MHz (DMSO-$_6$): δ10.6 (s, 1H), 9.2 (ds, 2H), 7.5–6.4 (m, 9H), 3.0–1.9(m, 13H), 2.2 (s, 3H), 1.0 (t, 3H). MS (TSP) m/z=430.5 (MH$^+$)

EXAMPLE 19

(±)-trans-2-Diethylaminothiocarbonyl-6-ethyl-3-methyl-8a-(3-methoxyphenyl)-o 4,4a,5,6,7,8,8a,9-octahydro-1H-pyrrolo[2,3-g]isoquinoline 1 g (2.4 mmol) of (±)-trans-2-diethylaminocarbonyl-6-ethyl-3-methyl-8a-(3-methoxyphenyl)-4,4a,5,6,7,8,8a,9-octahydro-1H-pyrrolo[2,3-g]isoquinoline prepared as described in example 1 and 0.48 g (1.2 mmol) of Lawesson reagent (Synthesis, 941, 1979) were dissolved in 50 ml of toluene. The solution was refluxed for 6 h. The solvent was evaporated in vacuo. The residue was treated with s.s. K$_2$CO$_3$ and extracted with AcOEt. The organic layers were dried over Na$_2$SO$_4$ and then the solvent evaporated in vacuo. The crude product was purified by flash chromatography (AcOEt/MeOH/conc. NH$_4$OH 80:20:2) yielding 0.5 g of the title compound. M.p.=156°–158° C.

$C_{26}H_{37}N_3OS$ I.R. (nujol): 1600, 1581, 1461, 1378 cm$^{-1}$. N.M.R. 300 MHz (CDCl$_3$): δ8.3 (s, 1H), 7.2–6.7 (m, 4H), 4.0–3.8 (m, 4H), 3.75 (s, 3H), 3.0–1.9 (m, 13H), 1.9 (s, 3H), 1.2 (t, 6H), 1.1(t, 3H). MS (TSP) m/z=440.6 (MH$^+$)

EXAMPLE 20

(±)-trans-2-Diethylaminothiocarbonyl-6, ethyl-8a-(3-hydroxyphenyl)-3-methyl-4,4a,5,6,7,8,8a,9-octahydro-1H-pyrrolo[2,3-g]isoquinoline 0.5 g of (±)-trans-2-diethylaminothiocarbonyl-6, ethyl-3-methyl-8a-(3-methoxyphenyl)-4,4a,5,6,7,8,8a,9-octahydro-1H-pyrrolo[2,3-g]isoquinoline were treated with 0.64 ml (6.8 mmol) of boron tribromide as described in example 2. The residue was purified by flash chromatography (EtOAc/MeOH/conc. NH$_4$OH 80:20:2) yielding 0.12 g of the title compound. M. p=243°–245° C.

$C_{25}H_{35}N_3OS$ I.R. (KBr): 3200, 2900, 1580, 1480 cm$^{-1}$ N.M.R. 300 MHz (DMSO-$_6$): δ10.2 (s, 1H), 9.2 (s, 1H), 7.1–6.4 (m, 4H), 3.9–3.7 (m, 6H), 3.0–1.75 (m, H), 1.8 (s, 3H), 1.1 (t, 6H), 0.9 (t, 3H). MS (TSP) m/z=426.3 (MH$^+$)

EXAMPLE 21

(±)-trans-6-Cyclopropylmethyl-2-diethylaminocarbonyl-8a-(3-methoxyphenyl)-3-methyl-4,4a,5,6,7,8,8a,9-octahydro-1H-pyrrolo[2,3-g]isoquinoline hydrochloride 0.28 g (0.80 mmol) of (±)-trans-2-cyclopropylmethyl-4a-(3-methoxyphenyl)-6-oxo-1,2,3,4,4a,5,6,7,8,8a-decahydroisoquinoline hydrochloride, 0.56 g (2.14 mmol) of N,N-diethyl-2-phenylhydrazono-3-oxobutyramide, 0.131 g (1.6 mmol) of CH$_3$COONa, 0.402 g (6.16 mmol) of zinc dust and 10 ml of glacial acetic acid were treated as described in example 1. The residue was purified by flash chromatography ((i-Pr)$_2$O/MeOH/conc. NH$_4$OH 90:10:0.5). The product was dissolved in acetone and the solution brought to acidic pH with Et$_2$O/HCl. The solid was filtered, washed and dried yielding 0.225 g of the title compound. M.p.=190°–195° C.

$C_{28}H_{39}N_3O_2$.HCl I.R. (KBr): 3400, 3200, 2915, 2580, 1715, 1600 cm$^{-1}$ N.M.R. 300 MHz (DMSO-$_6$): δ10.3 (bs, 1H), 10.2 (s, 1H), 7.3–6.7 (m, 4H), 3.7 (s, 3H), 3.6–2.5 (m, 14H), 2.5 (s, 3H), 2.1–1.4 (m, 4H), 1.0 (t, 6H), 0.6 (m, 2H), 0.4 (m, 2H). MS (EI) m/z=450.5 (MH$^+$)

EXAMPLE 22

(±)-trans-6-Cyclopropylmethyl-2-diethylaminocarbonyl-8a-(3-hydroxyphenyl)-3-methyl-4,4a,5,6,7,8,8a,9-octahydro-1H-pyrrolo[2,3-g]isoquinoline hydrochloride 0.225 g (0.46 mmol) of (±)-trans-6-cyclopropylmethyl-2-diethylaminocarbonyl-8a-(3-methoxyphenyl)-3-methyl-4,4a,5,6,7,8,8a,9-octahydro-1H-pyrrolo[2,3-g] isoquinoline were treated with 0.26 ml (2.76 mmol) of boron tribromide as described in example 2. The residue was purified by flash chromatography ((i-Pr)$_2$O/MeOH/conc. NH$_4$OH 75:25:0.5). The crude product was dissolved in acetone and the solution brought to acidic pH with HCl/Et$_2$O. The precipitate was titered yielding 0.07 g of the title compound. M.p.= 270°–272° C. dec.

C$_{27}$H$_{37}$N$_3$O$_2$·HCl I.R. (KBr): 3010, 2700, 1595, 1580 cm$^{-1}$ N.M.R. 300 MHz (DMSO-$_6$): δ10.4 (bs, 1H), 10.3 (s, 1H) 9.2 (s, 1H), 7.1–6.5 (m, 4H), 3.5–2.0 (m, 15H), 2.8 (s, 3H), 1.9 (s, 3H), 1.0 (t, 6H), 0.6 (m, 2H), 0.4(m,2H). MS (EI) m/z(free base)=435.3 (M$^+$)

EXAMPLE 23

(±)-trans-2-Diisopropylaminocarbonyl-6-ethyl-8a-(3-methoxyphenyl)-3-methyl-4,4a,5,6,7,8,8a,9-octahydro-1H-pyrrolo[2,3-g]isoquinoline 0.7 g (2.2 mmol) of (±)-trans-2-ethyl-4a-(3-methoxyphenyl)-6-oxo-1,2,3,4,4a,5,6,7,8,8a-decahydroisoquinoline hydrochloride, 2.0 g (7.0 mmol) of N, N-diisopropyl-2-phenylhydrazono-3-oxobutyramide, 0.575 g (7.0 mmol) of CH$_3$COONa, 1.83 g (28.0 mmol) of zinc dust and 3.5 ml of glacial acetic acid were treated as described in example 1 yielding 1.0 g of the title compound as an oil.

C$_{28}$H$_{41}$N$_3$O$_2$ I.R. (neat): 3250, 2960, 2580, 1740, 1600 cm$^{-1}$ N.M.R. 300 MHz (DMSO-$_6$) (hydrochloride): δ10.2 (s, 1H), 7.2–6.6 (m, 4H), 3.7 (s, 3H), 3.6–1.8 (m, 18H), 1.8 (s, 3H), 1.0 (d, 12H). MS (EI) mz=451.3 (M$^+$).

EXAMPLE 24

(±)-trans-2-Diisopropylaminocarbonyl-6-ethyl-8a-(3-hydroxyphenyl)-3-methyl-4,4a,5,6,7,8,8a,9-octahydro-1H-pyrrolo[2,3-g]isoquinoline hydrochloride 1.0 g (2.2 mmol) of (±)-trans-2-diisopropylaminocarbonyl-6-ethyl-8a-( 3-methoxyphenyl)-3-methyl-4,4a,5,6,7,8,8a,9-octahydro-1H-pyrrolo[2,3-g] isoquinoline were treated with 1.15 ml (12.0 mmol) of boron tribromide as described in example 2. The crude product was dissolved in MeOH and the solution brought to acidic pH with HCl/Et$_2$O. The solvent was evaporated in vacuo and the solid crystallized from acetone, yielding 0.5 g of the title compound. M.p.=263°–265° C.

C$_{27}$H$_{39}$N$_3$O$_2$·HCl I.R. (KBr): 3110, 2960, 1720, 1595, cm$^{-1}$ N.M.R. 300 MHz (DMSO-$_6$): δ10.4 (s, 1H), 10.3 (bs, 1H), 9.2 (s, 1H), 7.1–6.5 (m, 4H), 3.7–2.0 (m, 18H), 1.8 (s, 3H), 1.0 (d, 12H). MS (EI) m/z=437.3 (M$^+$).

EXAMPLE 25

(±)-trans-2-Aminocarbonyl-6-ethyl-8a-(3-methoxyphenyl)-3-methyl-4,4a,5,6,7,8,8a,9-octahydro-1H-pyrrolo[2,3-g]isoquinoline 3.24 g (10 mmol) of (±)-trans-2-ethyl-4a-(3-methoxyphenyl)-6-oxo-1,2,3,4,4a,5,6,7,8,8a-decahydroisoquinoline hydrochloride, 6.16 g (30.0 mmol) of 2-phenylhydrazono-3-oxobutyramide, 2.46 g (7.0 mmol) of CH$_3$COONa, 7.85 g (120.0 mmol) of zinc dust and 15 ml of glacial acetic acid were treated as described in example 1. The residue was purified by chromatography on silica gel (Et$_2$O-EtOAc/MeOH 0%→50%) yielding 3.0 g of oily product which was triturated in Et$_2$O yielding 2.5 g of the title compound. M.p.=176°–178° C.

C$_{22}$H$_{29}$N$_3$O$_2$ I.R. (neat): 3200, 2915, 2580, 1640, 1600, 1580 cm$^{-1}$ N.M.R. 300 MHz (DMSO-d$_6$): δ10.4 (s, 1H), 7.2–6.5 (m, 4H), 3.8 (s, 3H), 3.0–1.8 (m, 18H), 1.0 (t, 3H). MS (EI) m/z=368.1 (MH$_{30}$)

EXAMPLE 26

(±)-trans-2-Aminocarbonyl-6-ethyl-8a-(3-hydroxyphenyl)-3 -methyl-4,4a,5,6,7,8,8a,9-octahydro-1H-pyrrolo[2,3-g]isoquinoline hydrochloride 0.48 g (1.3 mmol) of (±)-trans-2-aminocarbonyl-6-ethyl-8a-(3-methoxyphenyl)-3-methyl-4,4a,5,6,7,8,8a,9-octahydro-1H-pyrrolo[2,3-g]isoquinoline were treated with 0.75 ml (7.8 mmol) of boron tribromide as described in example 2. The crude product was purified by chromatography on silica gel (CH$_2$Cl$_2$/MeOH 20%→30%). The residue was dissolved in MeOH and the solution brought to acidic pH with HCl/Et$_2$O. The solvent was evaporated in vacuo and the solid crystallized from acetone/MeOH, yielding 0.13 g of the title compound. M.p.=270°–273° C.

C$_{21}$H$_{27}$N$_3$O$_2$·HCl I.R. (KBr): 3160, 1645, 1595, 1450 cm$^{-1}$ N.M.R. 300 MHz (DMSO-$_6$): δ10.5 (s, 1H), 10.2 (bs, 1H), 7.2–6.5 (m, 4H), 3.7(m, 16H), 2.0 (s, 3H), 1.2 (t, 3H). MS (EI) m/z=354.1 (MH$^+$).

EXAMPLE 27

(±)-trans-6-Ethyl-2-ethoxycarbonyl-8a-(3-methoxyphenyl)-4,4a,5,6,7,8,8a,9-octahydro-3-trifluoromethyl-1H-pyrrolo[2,3-g]isoquinoline 3.24 g (10 mmol) of (±)-trans-2-ethyl-4a-(3-methoxyphenyl)-6-oxo-1,2,3,4,4a,5,6,7,8,8a-decahydroisoquinoline hydrochloride, 8.65 g (30 mmol) of ethyl 2-phenylhydrazono-4,4,4-trifluoro-3-oxobutyrate, 2.46 g (30 mmol) of CH$_3$COONa, 7.85 g (120 mmol) of zinc dust and 15 ml of glacial acetic acid were treated as described in example 1. The residue was purified by chromatography on silica gel EtOAc/MeOH 0%→10%) yielding 3.0 g of product which was triturated in Et$_2$O yielding 2.5 g of the title compound. M.p. 209°–211° C.

C$_{24}$H$_{29}$F$_3$N$_2$O$_3$ I.R. (neat): 3000, 1725, 1680, 1600 cm$^{-1}$ N.M.R. 300 MHz (DMSO-d$_6$) (hydrochloride): δ12.0 (s, 1H), 7.2–6.6 (m, 4H), 4.2 (q, 2H), 3.8 (s, 3H), 3.6–1.8 (m, 13H), 1.2 (t, 3H), 1.0 (t, 3H). MS (EI) m/z=451.1 (MH$^+$).

EXAMPLE 28

(±)-trans-6-Ethyl-2-ethoxycarbonyl-8a-(3-hydroxyphenyl)-4,4a,5,6,7,8,8a,9-octahydro-3-trifluoromethyl-1H-pyrrolo[2,3-g]isoquinoline hydrochloride 0.6 g (1.3 mmol) of (±)-trans-6-ethyl-2-ethoxycarbonyl-8a-(3-methoxyphenyl)-4,4a,5,6,7,8,8a,9-octahydro-3-trifluoromethyl-1H-pyrrolo[2,3-g]isoquinoline were treated with 0.75 ml (7.8 mmol) of boron tribromide as described in example 2. The crude product was purified by chromatography on silica gel (CH$_2$Cl$_2$/MeOH 20%→30%). The residue was dissolved in MeOH and the solution brought to acidic pH with HCl/Et$_2$O . The solvent was evaporated in vacuo and the solid was triturated in Et$_2$O, yielding 0.14 g of the title compound. M.p.=275°–278° C.

C$_{23}$H$_{27}$F$_3$N$_2$O$_3$·HCl I.R. (KBr): 3160, 2680, 1705, 1600, cm$^{-1}$ N.M.R. 300 MHz (DMSO-$_6$): δ12.1 (s, 1H), 10.4 (bs, 1H), 9.3 (s, 1H), 7.2–6.5 (m, 4H), 4.2 (q, 2H), 3.7–2.2 (m, 10H), 2.0 (s, 3H), 1.2 (m, 6H). MS (EI m/z=436.1 (M$^+$).

EXAMPLE 29

(±)-trans-2-Diethylaminocarbonyl-8a-(3-methoxyphenyl)-3-methyl-6-propyl-4,4a,5,6,7,8,8a, 9-octahydro-1H-pyrrolo[2,3-g]isoquinoline hydrochloride 0.37 g (0.86 mmol) of (±)-trans-2-diethylaminocarbonyl-ga-(3-methoxyphenyl)-3-methyl-4,4a,5,6,7,8,8a,9- octahydro-1H-pyrrolo[2,3-g]isoquinoline hydrochloride, 0.11 g (0.90 mmol) of propyl bromide, 0.24 g (1.71 mmol) of potassium carbonate and a catalytic amount of potassium iodide were dissolved in 5 ml of dimethylformamide and heated to 80° C. for 2 h. The solvent was evaporated in vacuo, the residue was taken up in $H_2O$ and extracted with EtOAc. The organic layer was separated, dried over $Na_2SO_4$ and the solvent removed in vacuo. The residue was dissolved in $Et_2O$ and the solution brought to acidic pH with $HCl/Et_2O$. The precipitate was filtered yielding 0.25 g of the title compound. M.p.=102°–106° C. dec.

$C_{27}H_{39}N_3O_2$.HCl I.R. (KBr): 3400, 3200, 2915, 2580, 1715, 1600 $cm^{-1}$

EXAMPLE 30

(±)-trans-2-Diethylaminocarbonyl-8a-(3-hydroxyphenyl)-3-methyl-6-propyl-4,4a,5,6,7,8,8a, 9-octahydro-1H-pyrrolo[2,3-g]isoquinoline hydrochloride 0.25 g (0.53 mmol) of (±)-trans-2-diethylaminocarbonyl-8a-(3-methoxyphenyl)-3-methyl-6, propyl-4,4a,5,6,7,8,8a, 9-octahydro-1H-pyrrolo[2,3-g]isoquinoline hydrochloride were treated with 0.3 ml (3.18 mmol) of boron tribromide as described in example 2. The crude product was dissolved in MeOH and the solution brought to acidic pH with $HCl/Et_2O$. The solvent was evaporated in vacuo and the solid crystallized from acetone, yielding 0.04 g of the title compound. M.p.=236°–238° C.

$C_{26}H_{37}N_3O_2$.HCl I.R. (KBr): 3130, 2915, 1590, 1460, $cm^{-1}$ N.M.R. 300 MHz (DMSO-$d_6$): δ10.2 (s, 1H), 9.0 (s, 1H), 7.2–6.4 (m, 4H), 3.7–2.2 (m, 12H), 2.0 (s, 3H), 1.8 (m, 2H), 1.6 (m, 2H), 1.0 (t, 6H), 0.8 (t, 6H), MS (EI) m/z=423.2 ($M^+$).

EXAMPLE 31

(±)-trans-2-Dimethylaminocarbonyl-6-ethyl-8a-(3-methoxyphenyl)-

3-methyl-4,4a,5,6,7,8,8a,9-octahydro-1H-pyrrolo[2,3-g] isoquinoline 1.0 g (3.1 mmol) of (±)-trans-2-ethyl-4a-(3-methoxyphenyl)-6-oxo-1,2,3,4,4a,5,6,7,8,8a-decahydroisoquinoline hydrochloride, 2.33 g (10 mmol) of N, N-dimethyl-2-phenylhydrazono-3-oxobutyramide, 0.82 g (1 0 mmol) of $CH_3COONa$, 2.6 g (40 mmol) of zinc dust and 5 ml of glacial acetic acid were treated as described in example 1. The residue was purified by chromatography on silica gel (EtOAc/MeOH 0%→30%) yielding 0.5 g of product which was crystallized from $Et_2O$ yielding 0.5 g of the title compound. M.p.=151°–153° C.

$C_{24}H_{33}N_3O_2$ I.R. (neat): 3210, 2910, 1585 $cm^{-1}$ N.M.R. 300 MHz (DMSO-$d_6$) (hydrochloride): δ10.3 (s, 1H), 7.2–6.6 (m, 4H), 3.8 (s, 3H), 3.6–1.8 (m, 22H), 1.0 (t, 3H). MS (EI) m/z=395.2 ($M^+$).

EXAMPLE 32

(±)-trans-2-Dimethylaminocarbonyl-6-ethyl-8a-(3-hydroxyphenyl)-3-methyl-4,4a,5,6,7,8,8a,9-octahydro-1H-pyrrolo[2,3-g]isoquinoline hydrochloride 0.5 g (1.25 mmol) of (±)trans-2-dimethylaminocarbonyl-6-ethyl-8a-(3-methoxyphenyl)-3-methyl-4,4a,5,6,7,8,8a,9-octahydro-1H-pyrrolo[2,3-g] isoquinoline were treated with 0.725 ml (7.5 mmol) of boron tribromide as described in example 2. The etude product was dissolved in MeOH and the solution brought to acidic pH with $HCl/Et_2O$. The solvent was evaporated in vacuo and the solid crystallized from EtOH, yielding 0.15 g of the title compound. M.p.= 305° C. dec.

$C_{23}H_{31}N_3O_2$.HCl I.R. (KBr): 3160, 1600, 1580 $cm^{-1}$ N.M.R. 300 MHz (DMSO-$_6$): δ10.4 (s, 1H), 10.2 (bs, 1H), 9.3 (s, 1H), 7.2–6.5 (m, 4H), 3.7–2.0 (m, 22H), 1.2 (t, 3H). MS (TSP) m/z=382.0 ($M^+$).

EXAMPLE 33

(−)-trans-2-Diethylaminocarbonyl-6-ethyl-8a-(3-methoxyphenyl)-3-methyl-4,4a,5,6,7,8,8a-octahydro-1H-pyrrolo[2,3-g]isoquinoline hydrochloride 1.9 g (5.87 mmol) of (−)-trans-2-ethyl-4a-(3-methoxyphenyl)-6-oxo-1,2,3,4,4a,5,6,7,8,8a-decahydroisoquinoline hydrochloride (Int. Pat. Appl. WO 93/01186), 4.61 g (17.61 mmol) of N,N-diethyl-2-phenylhydrazono-3-oxobutyramide, 1.45 g (17.61 mmol) of $CH_3COONa$, 1.9 g (29.35 mmol) of zinc dust and 15 ml of glacial acetic acid were treated as described in example 1. The residue was purified by flash chromatography ((i-Pr)$_2$O/MeOH/conc. $NH_4OH$ 75:25:0.5). The resulting solid was dissolved in acetone and the solution brought to acidic pH with $HCl/Et_2O$. The solvent was evaporated in vacuo and the solid triturated with $Et_2O$, yielding 2.3 g of the title compound. M.p.=201°–205° C.

$C_{26}H_{37}N_3O_2$.HCl I.R. (KBr): 3400, 3200, 2920, 1600 $cm^{-1}$ N.M.R. 300 MHz (DMSO-$d_6$): δ10.7 (bs, 1H), 10.4 (s, 1H), 7.3–6.7 (m, 4H), 3.7 (s, 3H), 3.6–2.5 (m, 17H), 1.8 (s, 3H), 1.2–1.0 (m, 9H) $[α]^{20}_D$=−20.32 (c=1, MeOH).

The I.R. and N.M.R. spectra were identical to those obtained for the racemate.

EXAMPLE 34

(−)-trans-2-Diethylaminocarbonyl-6-ethyl-8a-(3-hydroxyphenyl)-3-methyl-4,4a,5,6,7,8,8a,9-octahydro-1H-pyrrolo[2,3-g]isoquinoline hydrochloride 2.3 g (5.0 mmol) of (−)-trans-2-diethylaminocarbonyl-6-ethyl-8a-(3-methoxyphenyl)-3-methyl-4,4a,5,6,7,8,8a-octahydro-1H-pyrrolo[2,3-g]isoquinoline hydrochloride were treated with 2.9 ml (30 mmol) of boron tribromide as described in example 2. The crude product was dissolved in MeOH and the solution brought to acidic pH with $HCl/Et_2O$. The precipitate was filtered and crystallized from a mixture of acetone/MeOH=9/1, yielding 0.37g of the title compound. M.p.=239°–241° C.

$C_{25}H_{35}N_3O_2$.HCl I.R. (KBr): 3200, 2980, 2940, 1600 $cm^{-1}$ N.M.R. 300 MHz (DMSO-$_6$): δ10.4 (s, 1H), 7.3–6.7 (m, 4H), 3.6–2.5 (m, 17H), 1.8 (s, 3H), 1.2–1.0 (m, 9H) MS (EI)m/z=409.3 ($M^+$). $[α]^{20}_D$=−57.94 (c=1, MeOH).

The I.R. and N.M.R. spectra were identical to those obtained for the racemate.

EXAMPLE 35

(±)-trans-2-Diethylaminocarbonyl-6-ethyl-8a-(3-methoxyphenyl)-3-methyl-4,4a,5,6,7,8,8a-octahydro-1H-pyrrolo[2,3-g]isoquinoline hydrochloride 1.9 g (5.87 mmol) of (±)-trans-2-ethyl-4a-(3-methoxyphenyl)-6-oxo-1,2,3,4,4a,5,6,7,8,8a- decahydroisoquinoline hydrochloride (Int. Pat. Appl. WO 93/01186), 4.61 g (17.61 mmol) of N,N-diethyl-2-phenylhydrazono-3-oxobutyramide, 1.45 g (17.61 mmol) of $CH_3COONa$, 1.9 g (29.35 mmol) of zinc dust and 15 ml of glacial acetic acid were treated as described in example 1. The residue was purified by flash chromatography ((i-Pr)$_2$O/MeOH/conc. $NH_4OH$ 75:25:0.5). The resulting solid was dissolved in acetone and the solution brought to acidic pH with HCl/Et$_2$O. The solvent was evaporated in vacuo and the solid triturated with Et$_2$O, yielding 2.0 g of the title compound. M.p.=200°–204° C.

$C_{26}H_{37}N_3O_2 \cdot HCl$ I.R. (KBr): 3400, 3200, 2920, 1600 cm$^{-1}$ N.M.R. 300 MHz (DMSO-$d_6$): δ10.7 (bs, 1H), 10.4 (s, 1H), 7.3–6.7 (m, 4H), 3.7 (s, 3H), 3.6–2.5 (m, 17H), 1.8 (s, 3H), 1.2–1.0 (m, 9H) $[\alpha]^{20}_D$=+20.65 (c=1, MeOH).

The I.R. and N.M.R. spectra were identical to those obtained for the racemate.

EXAMPLE 36

(±)-trans-2-Diethylaminocarbonyl-6-ethyl-8a-(3-hydroxyphenyl)-3-methyl-4,4a,5,6,7,8,8a,9-octahydro-1H-pyrrolo[2,3-g]isoquinoline hydrochloride 2.0 g (4.3 mmol) of (+)-trans-2-diethylaminocarbonyl-6-ethyl-8a-(3-methoxyphenyl)-3-methyl-4,4a,5,6,7,8,8a-octahydro-1H-pyrrolo[2,3-g]isoquinoline hydrochloride were treated with 2.5 ml (25.8 mmol) of boron tribromide as described in example 2. The crude product was dissolved in MeOH and the solution brought to acidic pH with HCl/Et$_2$O. The precipitate was filtered and crystallized from a mixture of acetone/MeOH=9/1, yielding 0.28 g of the title compound. M.p.=239°–240° C.

$C_{25}H_{35}N_3O_2 \cdot HCl$ I.R. (KBr): 3200, 2980, 2940, 1600 cm$^{-1}$ N. M.R. 300 MHz (DMSO-$d_6$): δ10.6 (bs, 1H), 10.4 (s, 1H), 7.3–6.7 (m, 4H), 3.6–2.5 (m, 17H), 1.8 (s, 3H), 1.2–1.0 (m, 9H) MS (EI) m/z=409.2 (M$^+$). $[\alpha]^{20}_D$=+57.49 (c=1, MeOH).

The I.R. and N.M.R. spectra were identical to those obtained for the racemate.

EXAMPLE 37

(±)-trans-2-Diethylaminocarbonyl-6-(2-furylmethyl)-8a-(3-methoxyphenyl)-3-methyl-4,4a,5,6,7,8,8a,9-octahydro-1H-pyrrolo[2,3-g]isoquinoline hydrochloride 1.3 g (3.3 mmol) of (±)-trans-2-diethylaminocarbonyl-8a-(3-methoxyphenyl)-3-methyl-4,4a,5,6,7,8,8a,9-octahydro-1H-pyrrolo[2,3-g]isoquinoline, 0.28 ml (4.95 mmol) of acetic acid, 0.33 ml (3.96 mmol) of 2-furaldehyde were dissolved in 50 ml of MeOH under nitrogen atmosphere. 0.415 g (6.6 mmol) of sodium cyanoborohydride were added and the solution stirred for 15 h. Additional acetic acid (0.1 ml), 2-furaldehyde (0.3 ml) and sodium cyanoborohydride (0.2 g) were added. After two hours of stirring the reaction mixture was cooled to 0° C. and 50 ml of 5N hydrochloric acid were added. The solvent was removed in vacuo, the aqueous solution was extracted with Et$_2$O, the pH was adjusted to 8 with 20% NaOH and then extracted with AcOEt. The organic layer was dried over $Na_2SO_4$ and the solvent was removed in vacuo. The crude product was dissolved in acetone/MeOH and the solution brought to acidic pH with HCl/Et$_2$O. The precipitate was filtered, yielding 1.7 g of the title compound. M.p.=105° C. dec.

$C_{29}H_{37}N_3O_3 \cdot HCl$ I.R. (KBr): 3400, 3200, 2940, 1600 cm$^{-1}$ N.M.R. 300 MHz (DMSO-$d_6$): δ10.4 (s, 1H), 7.8–6.4 (m, 7H), 4.2 (s, 2H), 3.8 (s, 3H), 3.6–1.8 (m, 18H), 1.2–1.0 (m, 6H) MS (EI) m/z=475 (M$^+$).

EXAMPLE 38

(±)-trans-2-Diethylaminocarbonyl-6-(2-furylmethyl)-8a-(3-hydroxyphenyl)-3-methyl-4,4a,5,6,7,8,8a,9-octahydro-1H-pyrrolo[2,3-g]isoquinoline 1.7 g (3.32 mmol) of (±)-trans-2-dimethylaminocarbonyl-6-(2-furylmethyl)-8a-(3-methoxyphenyl)-3-methyl-4,4a,5,6,7,8,8a,9-octahydro-1H-pyrrolo[2,3-g] isoquinoline hydrochloride were treated with 1.86 ml (19.9 mmol) of boron tribromide as described in example 2. The residue was purified by flash chromatography (EtOAc/MeOH/conc. $NH_4OH$ 95:5:0.5). The solid was triturated with acetone, yielding 0.07 g of the title compound. M.p.=215°–216° C. dec.

$C_{28}H_{35}N_3O_3$ I.R. (KBr): 3340, 2930, 2900, 1590 cm$^{-1}$ N.M.R. 300 MHz (DMSO-$d_6$): δ10.4 (s, 1H), 9.2 (s, 1H), 7.5 (s, 2H), 7.1–6.2 (m, 6H), 3.5–1.8 (m, 19H), 1.0 (t, 6H). MS (EI) m/z=461.1 (M$^+$).

EXAMPLE 39

(±)-trans-2-Diethylaminocarbonyl-8a-(3-methoxyphenyl)-3-methyl-4,4a,5,6,7,8,8a-octahydro-1H-pyrrolo[2,3-g]isoquinoline 1.6 g (5.7 mmol) of (±)-trans-4a-(3-methoxyphenyl)-6-oxo-1,2,3,4,4a,5,6,7,8,8a-decahydroisoquinoline hydrochloride, 6.0 g (22.8 mmol) of N,N-diethyl-2-phenylhydrazono-3-oxobutyramide, 1.9 g (22.8 mmol) of $CH_3COONa$, 2.2 g (34.2 mmol) of zinc dust and 30 ml of glacial acetic acid were treated as described in example 1, yielding 1.3 g of the title compound. M.p.=197°–199° C.

$C_{24}H_{33}N_3O_2$ I.R. (KBr): 3270, 2915, 1605 cm$^{-1}$

EXAMPLE 40

(±)-trans-6-Butyl-2-diethylaminocarbonyl-8a-(3-methoxyphenyl)-3-methyl-4,4a,5,6,7,8,8a-octahydro-1H-pyrrolo[2,3-g]isoquinoline 0.2 g (0.57 mmol) of (±)-trans-2-butyl-4a-(3-methoxyphenyl)-6-oxo-1,2,3,4,4a,5,6,7,8,8a-decahydroisoquinoline hydrochloride, 0.45 g (1.71 mmol) of N,N-diethyl-2-phenylhydrazono-3-oxobutyramide, 0.14 g (1.71 mmol) of $CH_3COONa$, 0.22 g (3.42 mmol) of zinc dust and 5 ml of glacial acetic acid were treated as described in example 1, yielding 0.15 g of the title compound. M.p.= 134° C. dec.

$C_{28}H_{41}N_3O_2$ I.R. (KBr) (hydrochloride): 3200, 2960, 2925, 1630, 1600 cm$^{-1}$

EXAMPLE 41

(±)-trans-6-Butyl-2-diethylaminocarbonyl-8a-(3-hydroxyphenyl)-3-methyl-4,4a,5,6,7,8,8a-octahydro-1H-pyrrolo[2,3-g]isoquinoline 0.15 g (0.31 mmol) of (±)-trans-6-butyl-2-diethylaminocarbonyl-8a-(3-methoxyphenyl)-3-methyl-4,4a,5,6,7,8,8a-octahydro-1H-pyrrolo[2,3-g]isoquinoline were treated with 0.174 ml (1.86 mmol) of boron tribromide as described in example 2, yielding 0.06 g of the title compound. M.p.=228°–229° C.

$C_{27}H_{39}N_3O_2$ I.R. (KBr): 3330, 2920, 1590 cm$^{-1}$

EXAMPLE 42

(±)-trans-7-Ethyl-4a-(3-methoxyphenyl)-1-methyl-4,4a,5,6,7,8,8a,9-octahydro-2-phenyl-1H-imidazo[4,5-g]isoquinoline A solution of 0.46 g (2.98 mmol) of N-methylbenzimidoyl chloride (J. Am. Chem. Soc., 1962, 84, 769) in 12 ml of THF was cooled to -78° C. under nitrogen atmosphere and 0.73 ml (5.21 mmol) of triethylamine were added. After 30 min a solution of 0.45 g (1.49 mmol) of (±)-trans-2-ethyl-6-hydroxyimino-4a-(3-methoxyphenyl)-1,2,3,4,4a,5,6,7,8,8a-decahydroisoquinoline in 3 ml of THF was added. The reaction mixture was allowed to warm to room temperature and then refluxed for 5 h. Water was added and the mixture was extracted with $CH_2Cl_2$. The organic layer was washed with brine and dried. The solvent was removed in vacuo and the resulting product was dissolved in 25 ml of toluene, 0.99 g of p-toluenesulphonic acid were added and the reaction mixture was heated to reflux in a Dean-Stark apparatus for 6 h. The solvent was removed in vacuo, the residue was taken up in water, the pH adjusted to 10 with 1N NaOH. The aqueous layer was extracted with $CH_2Cl_2$, the organic layer was dried and the solvent was removed in vacuo. The crude product was purified by flash chromatography (EtOAc/MeOH/conc. $NH_4OH$ 85:15:2) yielding 0.276 g of the title compound. M.p.=146°–150° C.

$C_{26}H_{31}N_3O$ I.R. (KBr): 2920, 1600, 1580 cm$^{-1}$ N.M.R. 300 MHz (DMSO-$d_6$): δ7.6–6.6 (m, 9H), 3.8 (s, 3H), 3.5 (s, 3H), 3.0–1.6 (m, 13H), 1.0 (t, 3H). MS (IE) m/z=401.2 (M$^+$).

EXAMPLE 43

(±)-trans-7-Ethyl-4a-(3-hydroxyphenyl)-1-methyl-4,4a,5,6,7,8,8a,9-octahydro-2-phenyl-1H-imidazo[4,5-g]isoquinoline 0.27 g (0.67 mmol) of (±)-trans-7-ethyl-4a-(3-methoxyphenyl)-1-methyl-4,4a,5,6,7,8,8a,9-octahydro-2-phenyl-1H-imidazo[4,5-g]isoquinoline were treated with 0.38 ml (4.02 mmol) of boron tribromide as described in example 2. The residue was purified by flash chromatography (EtOAc/MeOH/conc. $NH_4OH$ 80:20:2). The resulting solid was crystallized from acetone, yielding 0.13 g of the title compound. M.p.=249°–251° C.

$C_{25}H_{29}N_3O$ I.R. (KBr): 3400, 2940, 1595, 1450 cm$^{-1}$ N.M.R. 300 MHz (DMSO-$_6$): δ9.1 (s, 1H), 7.8–6.4 (m, 9H), 3.5 (s, 3H), 3.0–1.6 (m, 13H), 1.0 (t, 3H). MS (EI) m/z= 387.2 (M$^+$).

EXAMPLE 44

(±)-trans-6-Ethyl-8a-(3-methoxyphenyl)-3-methyl-2-pyrrolidinocarbonyl-4,4a,5,6,7,8,8a,9-octahydro-1H-pyrrolo[2,3-g]isoquinoline hydrochloride 1 g (3.1 mmol) of (±)-trans-2-ethyl-4a-(3-methoxyphenyl)-6-oxo-1,2,3,4,4a,5,6,7,8,8a-decahydroisoquinoline hydrochloride, 2.4 g (9.3 mmol) of 1-(2-phenylhydrazono-3-oxobutyryl)pyrrolidine, 0.76 g (9.3 mmol) of $CH_3COONa$, 2.4 g (37.2 mmol) of zinc dust and 10 ml of glacial acetic acid were treated as described in example 1. The crude product was purified by flash chromatography EtOAc/MeOH/conc. $NH_4OH$ 80:20:0.5). The residue was dissolved in acetone and the solution brought to acidic pH with HCl/$Et_2O$. The precipitate was filtered, yielding 0.63 g of the title compound. M.p.=127°–131° C.

$C_{26}H_{35}N_3O_2$·HCl I.R. (K.Br): 3280, 2940, 1610, 1580 cm$^{-1}$.

EXAMPLE 45

(±)-trans-6-Ethyl-8a-(3-hydroxyphenyl)-3-methyl-2-pyrrolidinocarbonyl-4,4a,5,6,7,8,8a,9-octahydro-1H-pyrrolo[2,3-g]isoquinoline 0.63 g (1.37 mmol) of (±)-trans-6-ethyl-8a-(3-methoxyphenyl)-3-methyl-2-pyrrolidinocarbonyl-4,4a,5,6,7,8,8a,9-octahydro-1H-pyrrolo[2,3-g]isoquinoline were treated with 0.77 ml (8.22 mmol) of boron tribromide as described in example 2. The residue was purified by flash chromatography (EtOAc/MeOH/conc. $NH_4OH$ 80:20:0.5). The resulting solid was triturated with $Et_2O$, yielding 0.13 g of the title compound. M.p.=224°–226° C.

$C_{25}H_{33}N_3O_2$ I.R. (KBr): 3400, 2940, 1595, 1450 cm$^{-1}$

EXAMPLE 46

(±)-trans-2-Diisopropylaminocarbonyl-8a-(3-methoxyphenyl)-3-methyl-6-propyl-4,4a,5,6,7,8,8a-octahydro-1H-pyrrolo[2,3-g]isoquinoline hydrochloride 0.34 g (0.74 mmol) of (±)-trans-2-diisopropylaminocarbonyl-8a-(3-methoxyphenyl)-3-methyl-4,4a,5,6,7,8,8a,9-octahydro-1H-pyrrolo[2,3-g]isoquinoline hydrochloride, 0.095 g (0.78 mmol) of propyl bromide, 0.204 g (1.48 mmol) of potassium carbonate and a catalytic amount of potassium iodide in 5 ml of dimethylformamide were treated as described in example 29. The residue was dissolved in $Et_2O$ and the solution brought to acidic pH with HCl/$Et_2O$. The precipitate was filtered yielding 0.22 g of the title compound. M.p.=150° C. dec.

$C_{29}H_{43}N_3O_2$·HCl I.R. (KBr): 3400, 3200, 2915, 2580, 1600 cm$^-$

EXAMPLE 47

(±)-trans-2-Diisopropylaminocarbonyl-8a-(3-hydroxyphenyl)-3-methyl-6-propyl-4,4a,5,6,7,8,8a-octahydro-1H-pyrrolo[2,3-g]isoquinoline hydrochloride 0.22 g (0.44 mmol) of (±)-trans-2-diisopropylaminocarbonyl-8a-(3-methoxyphenyl)-3-methyl-6-propyl-4,4a,5,6,7,8,8a-octahydro-1H-pyrrolo[2,3-g]isoquinoline hydrochloride were treated with 0.25 ml (2.64 mmol) of boron tribromide as described in example 2. The residue was purified by flash chromatography (EtOAc/MeOH/conc. $NH_4OH$ 80:20:0.5). The residue was dissolved in acetone and the solution brought to acidic pH with HCl/$Et_2O$. The precipitate was filtered yielding 0.055 g of the title compound. M.p.=240°–243° C.

$C_{28}H_{41}N_3O_2$·HCl I.R. (KBr): 3400, 2940, 1595, 1450 cm$^{-1}$

CHEMICAL TABLE
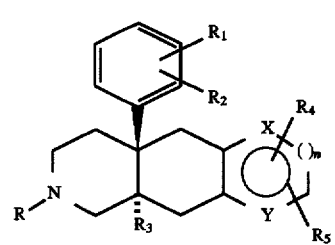
| Ex. n. | R | $R_1$ | $R_2$ | $R_3$ | $R_4$ | $R_5$ | * | Molecular formula | M.P. °C. |
|---|---|---|---|---|---|---|---|---|---|
| 1 | Et | m-OMe | H | H | $CONEt_2$ | Me | (±) | $C_{26}H_{37}N_3O_2$ | 247 dec. (as .HCl) |
| 2 | Et | m-OH | H | H | $CONEt_2$ | Me | (±) | $C_{25}H_{35}N_3O_2$ | 221–223 |
| 3 | Et | m-OMe | H | H | COOEt | Me | (±) | $C_{24}H_{32}N_2O_3$ | — |
| 4 | Et | m-OH | H | H | COOEt | Me | (±) | $C_{23}H_{30}N_2O_3 \cdot 0.5H_2O$ | 195–197 |
| 5 | Et | m-OMe | H | H | $CON\text{-}n\text{-}Pr_2$ | Me | (±) | $C_{28}H_{41}N_3O_2 \cdot HCl$ | 250 dec. |
| 6 | Et | m-OH | H | H | $CON\text{-}n\text{-}Pr_2$ | Me | (±) | $C_{27}H_{39}N_3O_2$ | 151–153 |
| 7 | Et | m-OMe | H | H | COO-i-Bu | Me | (±) | $C_{26}H_{36}N_2O_3 \cdot HCl$ | 230 dec. |

CHEMICAL TABLE
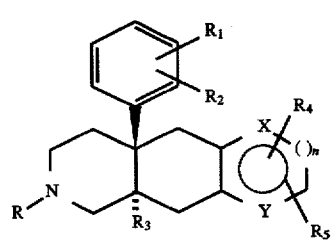
| Ex. n. | R | $R_1$ | $R_2$ | $R_3$ | $R_4$ | $R_5$ | | * | Molecular formula | M.P. °C. |
|---|---|---|---|---|---|---|---|---|---|---|
| 8 | Et | m-OH | H | H | COOi-Bu | Me | NH, $R_4$, $R_5$ | (±) | $C_{25}H_{34}N_2O_3$ | 196–198 |
| 9 | Me | m-OMe | H | H | $CONEt_2$ | Me | NH, $R_4$, $R_5$ | (±) | $C_{25}H_{35}N_3O_2$ | 250 dec. (as .HCl) |
| 10 | Me | m-OH | H | H | $CONEt_2$ | Me | NH, $R_4$, $R_5$ | (±) | $C_{24}H_{33}N_3O_2$.HCl | >250 |
| 11 | Me | m-OMe | H | H | $CONEt_2$ | Me | $R_5$, $R_4$, NH | (±) | $C_{25}H_{35}N_3O_2$ | 153–155 |
| 12 | Me | m-OH | H | H | $CONEt_2$ | Me | $R_5$, $R_4$, NH | (±) | $C_{24}H_{33}N_3O_2$ | 235–238 |
| 13 | Me | m-OMe | H | H | $CONHCH_2Ph$ | Me | NH, $R_4$, $R_5$ | (±) | $C_{28}H_{33}N_3O_2$ | 162–164 |
| 14 | Me | m-OH | H | H | $CONHCH_2Ph$ | Me | NH, $R_4$, $R_5$ | (±) | $C_{27}H_{31}N_3O_2$.HCl | 297–299 |

CHEMICAL TABLE
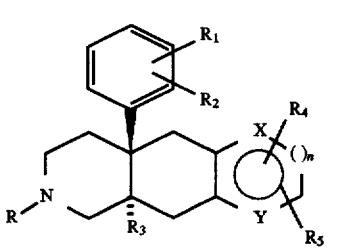
I
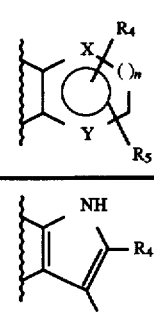
| Ex. n. | R | $R_1$ | $R_2$ | $R_3$ | $R_4$ | $R_5$ | [ring] | * | Molecular formula | M.P. °C. |
|---|---|---|---|---|---|---|---|---|---|---|
| 15 | Me | m-OMe | H | H | $CON(-CH_2-)_4$ | Me | 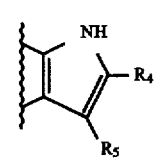 | (±) | $C_{25}H_{33}N_3O_2$ | 171–173 |
| 16 | Me | m-OH | H | H | $CON(-CH_2-)_4$ | Me | 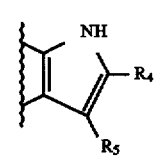 | (±) | $C_{24}H_{31}N_3O_2 \cdot HCl$ | 230–233 |
| 17 | Et | m-OMe | H | H | CONHPh | Me | 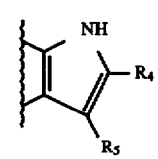 | (±) | $C_{28}H_{33}N_3O_2$ | 178–180 |
| 18 | Et | m-OH | H | H | CONHPh | Me | 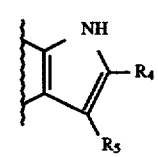 | (±) | $C_{27}H_{31}N_3O_2 \cdot HCl$ | 271–272 |
| 19 | Et | m-OMe | H | H | $CSNEt_2$ | Me | 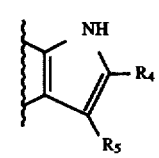 | (±) | $C_{26}H_{37}N_3OS$ | 156–158 |
| 20 | Et | m-OH | H | H | $CSNEt_2$ | Me | 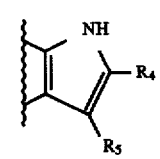 | (±) | $C_{25}H_{35}N_3OS$ | 243–245 |
| 21 | CPM | m-OMe | H | H | $CONEt_2$ | Me | | (±) | $C_{28}H_{39}N_3O_2 \cdot HCl$ | 190–195 |

CHEMICAL TABLE

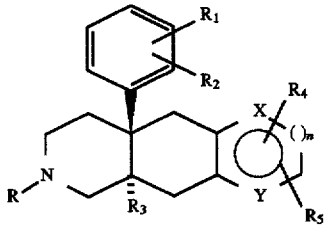

| Ex. n. | R | $R_1$ | $R_2$ | $R_3$ | $R_4$ | $R_5$ | | * | Molecular formula | M.P. °C. |
|---|---|---|---|---|---|---|---|---|---|---|
| 22 | CPM | m-OH | H | H | $CONEt_2$ | Me | NH, $R_4$, $R_5$ | (±) | $C_{27}H_{37}N_3O_2 \cdot HCl$ | 270–272 dec |
| 23 | Et | m-OMe | H | H | $CON(i-Pr)_2$ | Me | NH, $R_4$, $R_5$ | (±) | $C_{28}H_{41}N_3O_2$ | oil |
| 24 | Et | m-OH | H | H | $CON(i-Pr)_2$ | Me | NH, $R_4$, $R_5$ | (±) | $C_{27}H_{39}N_3O_2 \cdot HCl$ | 263–265 |
| 25 | Et | m-OMe | H | H | $CONH_2$ | Me | NH, $R_4$, $R_5$ | (±) | $C_{22}H_{29}N_3O_2$ | 176–178 |
| 26 | Et | m-OH | H | H | $CONH_2$ | Me | NH, $R_4$, $R_5$ | (±) | $C_{21}H_{27}N_3O_2 \cdot HCl$ | 270–273 |
| 27 | Et | m-OMe | H | H | COOEt | $CF_3$ | NH, $R_4$, $R_5$ | (±) | $C_{24}H_{29}F_3N_2O_3$ | 209–211 |
| 28 | Et | m-OH | H | H | COOEt | $CF_3$ | NH, $R_4$, $R_5$ | (±) | $C_{23}H_{27}F_3N_2O_3 \cdot HCl$ | 275–278 |

-continued
CHEMICAL TABLE
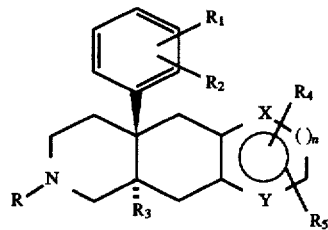
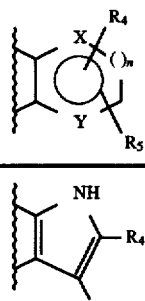
| Ex. n. | R | $R_1$ | $R_2$ | $R_3$ | $R_4$ | $R_5$ | | * | Molecular formula | M.P. °C. |
|---|---|---|---|---|---|---|---|---|---|---|
| 29 | n-Pr | m-OMe | H | H | $CONEt_2$ | Me | NH | (±) | $C_{27}H_{39}N_3O_2.HCl$ | 102–106 dec. |
| 30 | n-Pr | m-OH | H | H | $CONEt_2$ | Me | NH | (±) | $C_{26}H_{37}N_3O_2.HCl$ | 236–238 |
| 31 | Et | m-OMe | H | H | $CONMe_2$ | Me | NH | (±) | $C_{24}H_{33}N_3O_2$ | 151–153 |
| 32 | Et | m-OH | H | H | $CONMe_2$ | Me | NH | (±) | $C_{23}H_{31}N_3O_2.HCl$ | 305 dec. |
| 33 | Et | m-OMe | H | H | $CONEt_2$ | Me | NH | (−) | $C_{26}H_{37}N_3O_2.HCl$ | 201–205 |
| 34 | Et | m-OH | H | H | $CONEt_2$ | Me | NH | (−) | $C_{25}H_{35}N_3O_2.HCl$ | 239–241 |
| 35 | Et | m-OMe | H | H | $CONEt_2$ | Me | NH | (+) | $C_{26}H_{37}N_3O_2.HCl$ | 200–204 |

-continued

CHEMICAL TABLE

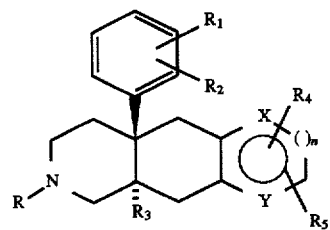

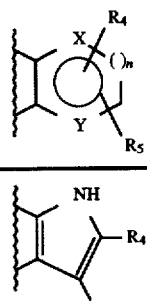

| Ex. n. | R | $R_1$ | $R_2$ | $R_3$ | $R_4$ | $R_5$ | | * | Molecular formula | M.P. °C. |
|---|---|---|---|---|---|---|---|---|---|---|
| 36 | Et | m-OH | H | H | $CONEt_2$ | Me | NH, $R_4$, $R_5$ | (+) | $C_{25}H_{35}N_3O_2 \cdot HCl$ | 239–240 |
| 37 | 2-furyl methyl | m-OMe | H | H | $CONEt_2$ | Me | NH, $R_4$, $R_5$ | (±) | $C_{29}H_{37}N_3O_3 \cdot HCl$ | 105 dec. |
| 38 | 2-furyl methyl | m-OH | H | H | $CONEt_2$ | Me | NH, $R_4$, $R_5$ | (±) | $C_{28}H_{35}N_3O_3$ | 215–216 dec. |
| 39 | H | m-OMe | H | H | $CONEt_2$ | Me | NH, $R_4$, $R_5$ | (±) | $C_{24}H_{33}N_3O_2$ | 197–199 |
| 40 | n-Bu | m-OMe | H | H | $CONEt_2$ | Me | NH, $R_4$, $R_5$ | (±) | $C_{28}H_{41}N_3O_2$ | 134 dec. |
| 41 | n-Bu | m-OH | H | H | $CONEt_2$ | Me | NH, $R_4$, $R_5$ | (±) | $C_{27}H_{39}N_3O_2$ | 228–229 |
| 42 | Et | m-OMe | H | H | Ph | Me | N, $R_4$, N, $R_5$ | (±) | $C_{26}H_{31}N_3O$ | 146–150 |

-continued
CHEMICAL TABLE

I

| Ex. n. | R | $R_1$ | $R_2$ | $R_3$ | $R_4$ | $R_5$ | | * | Molecular formula | M.P. °C. |
|---|---|---|---|---|---|---|---|---|---|---|
| 43 | Et | m-OH | H | H | Ph | Me | (ring with N, $R_4$, N-$R_5$) | (±) | $C_{25}H_{29}N_3O$ | 249–251 |
| 44 | Et | m-OMe | H | H | $CON(-CH_2-)_4$ | Me | (ring with NH, $R_4$, $R_5$) | (±) | $C_{26}H_{35}N_3O_2 \cdot HCl$ | 127–131 |
| 45 | Et | m-OH | H | H | $CON(-CH_2-)_4$ | Me | (ring with NH, $R_4$, $R_5$) | (±) | $C_{25}H_{33}N_3O_2$ | 224–226 |
| 46 | n-Pr | m-OMe | H | H | $CON(i-Pr)_2$ | Me | (ring with NH, $R_4$, $R_5$) | (±) | $C_{29}H_{43}N_3O_2 \cdot HCl$ | 150 dec. |
| 47 | n-Pr | m-OH | H | H | $CON(i-Pr)_2$ | Me | (ring with NH, $R_4$, $R_5$) | (±) | $C_{28}H_{41}N_3O_2 \cdot HCl$ | 240–243 |

PHARMACOLOGICAL METHODS AND RESULTS

OPIOID RADIOLIGAND BINDING ASSAYS

Mouse brain membranes were prepared as described by Kosterlitz (*Br. J. Pharmacol.*, 1981, 73, 939.). The binding of the preferential delta ligand [$^3$H] -[D-Ala$^2$, D-Leu$^5$]-enkephalin (DADLE) was evaluated at its $K_D$ concentration (1.3 nM) in presence of 40 nM of the unlabelled mu ligand [D-Ala$^2$, MePhe$^4$, Gly-ol$^5$]-enkephalin (DAMGO). The binding of the mu ligand [$^3$H]-DAMGO (*Eur. J. Pharmacol.*, 1989, 166, 213) and of the kappa ligand [$^3$H]-U69593 (*Excerpta Medica*, 1990, 211) were carried out at 0.5 nM. The non-specific binding was determined in presence of naloxone (10 µM) for all tritiated ligands. Binding data were expressed as percentage of inhibition and fitted the following equation: $f(x)=100 \cdot X/(IC_{50}+X)$ where X are cold drug concentration values. The $IC_{50}$ obtained were used to calculate the inhibitory constants ($K_i$) accordingly to the Cheng and Prusoff relation (*Biochem. Pharmacol.*, 1973, 22, 3099).

MOUSE VAS DEFERENS (MVD) BIOASSAYS

Vasa deferentia were obtained from CD-1 mice and were suspended in a Mg$^{2+}$-free Krebs buffer at 37° C. For the delta agonist/antagonist studies, the tissues were electrically stimulated with pulse trains having the following parameters: train duration 50 ms, stimulus duration 2 ms, frequency of stimuli 50 Hz, maximal voltage 60–70 V, train frequency 0.1 Hz. Concentration response curves for each compounds were constructed cumulatively. Linear regression analysis and $IC_{50}$ concentrations were evaluated according to Tallarida and Murray (*Manual of Pharmacological Calculations*, Springer Verlag N.Y., 1981).

The most potent compounds described in the present invention showed affinities for the delta receptor ranging from 0.5 to 200 nM with delta selectivity ranging from 30 to 1500 times in respect to the other opioid receptor types. These compounds displayed also potent delta agonist and antagonist properties in the MVD preparation. Selective delta agonists (antagonised by the selective delta antagonist naltrindole) displayed $IC_{50}$s ranging from 1 to 500 nM. For example, compound of example 34 shows a Ki delta=0.73 nM, Ki mu/Ki delta=110 and Ki kappa/Ki delta=1105 and an $IC_{50}$=26 nM in the MVD preparation. Selective delta antagonists showed $K_{e}$, against DADLE ranging from 1 to 50 nM. For example, compound of example 10 shows a Ki delta=2.15 nM, Ki mu/Ki delta=45 and Ki kappa/Ki delta=403 and a $K_e$=7 nM against DADLE in the MVD preparation.

Mouse abdominal constriction (MAC) (*Proc. Soc. Exp. Biol. Med.*, 1957, 95, 729), mouse tail-flick (MTF) (*J. Pharm. Exp. Ther.*, 1941, 72, 74) and mouse tail-flick warm water (MTF-WW) (*Life Sci.*, 1986, 39, 1795) were adopted to evaluate the antinociceptive efficacy of the compounds of the present invention.

We claims:

1. A compound, or solvate or salt thereof, of formula (I):

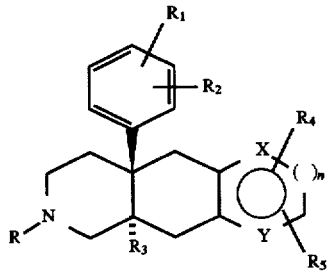

wherein:

R is hydrogen or a straight or branched $C_1$–$C_5$ alkyl, $C_3$–$C_7$ cycloalkyl, $C_4$–$C_6$cycloalkylalkyl, $C_3$–$C_5$ alkenyl, aryl, aralkyl or furan-2-yloalkyl;

$R_1$ and $R_2$, which can be the same or different, are each hydrogen, hydroxy, $C_1$–$C_3$alkoxy, halogen, SH, $C_1$–$C_4$-alkylthio, $NHR_6$, $NR_6R_7$, $NHCOR_6$, $NHSO_2R_6$, wherein $R_6$ and $R_7$, which are the same or different, are hydrogen or $C_1$–$C_6$ alkyl;

$R_3$ is hydrogen, hydroxy or $C_1$–$C_3$ alkoxy;

$R_4$ is a

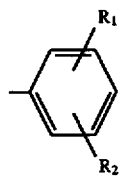

group ($R_1$ and $R_2$ having the meanings defined above) or a -C(Z)-$R_8$ group, in which Z is oxygen or sulphur, and $R_8$ is $C_1$–$C_{18}$-alkyl, $C_1$–$C_{18}$-alkoxy or $NR_9R_{10}$, wherein $R_9$ and $R_{10}$, which may be the same or different, are hydrogen, straight or branched $C_1$–$C_6$ alkyl, $C_3$–$C_7$ cycloalkyl, $C_4$–$C_6$ cycloalkylalkyl, $C_3$–$C_6$ alkenyl, aryl, aralkyl or an optionally substituted heterocyclic ring or, taken together with the nitrogen atom which they are linked to, they form an alkylene chain having from 2 to 5 carbon atoms, optionally interrupted by an oxygen or nitrogen atom;

or $R_4$ is a group

in which $R_{11}$ and $R_{12}$ are the same as $R_9$ and $R_{10}$ respectively, and Z is as defined above;

$R_5$ is hydrogen, $C_1$–$C_{18}$ alkyl, $C_2$–$C_{18}$ alkenyl, trifluoromethyl or is a

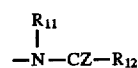

group ($R_1$ and $R_2$ having the meanings defined above);

n is zero 1;

one of X or Y is NH, and the other is CH or a $R_4$- or R5-substituted carbon atom.

2. A compound according to claim 1 in which R is methyl, ethyl, cyclopropylmethyl, propyl, 2-phenylethyl or 2-furylmethyl.

3. A compound according to claim 1 or in which each of $R_1$ and $R_2$ is hydrogen, hydroxy, methoxy, chlorine, bromine, fluorine, SH, methylthio, amino, methylamino, ethylamino, dimethylamino, diethylamino, diisopropylamino, methylisopropylamino, acetylamino or sulfonylamino, at any position of the ring.

4. A compound according to claim 1 which $R_5$ is hydrogen, methyl, ethyl, propyl, butyl, hexyl, octyl, decyl, dodecyl, octadecyl, allyl, trifluoromethyl or phenyl.

5. A compound according to any claim 1 which $R_4$ is ethoxycarbonyl, i-butyloxycarbonyl, aminocarbonyl, dimethylaminocarbonyl, diethylaminocarbonyl, di-n-propylaminocarbonyl, di-i-propylaminocarbonyl, pyrrolidinocarbonyl, benzylaminocarbonyl, phenylaminocarbonyl, morpholinocarbonyl, N-ethyl-N-i-isopropylaminocarbonyl, diethylaminothiocarbonyl, or phenyl.

6. A compound selected from:

(±)-trans-2-Diethylaminocarbonyl-6-ethyl-8a-(3-methoxyphenyl)-3-methyl-4,4a,5,6,7,8,8a-octahydro-1H-pyrrolo[2,3-g]isoquinoline;

(±)-trans-2-Diethylaminocarbonyl-6-ethyl-8a-(3-hydroxyphenyl)-3-methyl-4,4a,5,6,7,8,8a,9-octahydro-1H-pyrrolo[2,3-g]isoquinoline;

(±)-trans-6-Ethyl-2-ethoxycarbonyl-3-methyl-8a-(3-methoxyphenyl)-4,4a,5,6,7,8,8a,9-octahydro-1H-pyrrolo[2,3-g]isoquinoline;

(±)-trans-6-Ethyl-2-ethoxycarbonyl-8a-(3-hydroxyphenyl)-3-methyl-4,4a,5,6,7,8,8a,9-octahydro-1H-pyrrolo[2,3-g]isoquinoline; p1 (±)-trans-Dipropylaminocarbonyl-6-ethyl-3-methyl-8a-(3-methoxyphenyl)-4,4a,5,6,7,8,8a,9-octahydro-1H-pyrrolo[2,3-g]isoquinoline hydrochloride;

(±)-trans-Dipropylaminocarbonyl-6-ethyl-8a-(3-hydroxyphenyl)-3-methyl-4,4a,5,6,7,8,8a,9-octahydro-1H-pyrrolo[2,3-g]isoquinoline;

(±)-trans-2-(i-Butoxycarbonyl)-6-ethyl-3-methyl-8a-(3-methoxyphenyl)-4,4a,5,6,7,8,8a,9-octahydro-1H-pyrrolo[2,3-g]isoquinoline hydrochloride;

(±)-trans-2-(i-Butoxycarbonyl)-6-ethyl-8a-(3-hydroxyphenyl)-3-methyl-4,4a,5,6,7,8,8a,9-octahydro-1H-pyrrolo[2,3-g]isoquinoline hydrochloride;

(±)-trans-2-Diethylaminocarbonyl-3,6-dimethyl-8a-(3-methoxyphenyl)-4,4a,5,6,7,8,8a,9-octahydro-1H-pyrrolo[2,3-g]isoquinoline;

(±)-trans-2-Diethylaminocarbonyl-3,6-dimethyl-8a-(3-hydroxyphenyl)-4,4a,5,6,7,8,8a,9-octahydro-1H-pyrrolo[2,3-g]isoquinoline hydrochloride;

(±)-trans-2-Diethylaminocarbonyl-3,7-dimethyl-4a-(3-methoxyphenyl)-4,4a,5,6,7,8,8a,9-octahydro-1H-pyrrolo[3,2-g]isoquinoline;

(±)-trans-2-Diethylaminocarbonyl-3,7-dimethyl-4a-(3-hydroxyphenyl)-4,4a,5,6,7,8,8a,9-octahydro-1H-pyrrolo[3,2-g]isoquinoline;

(±)-trans-2-Benzylaminocarbonyl-3,6-dimethyl-8a-(3-methoxyphenyl)-4,4a,5,6,7,8,8a,9-octahydro-1H-pyrrolo[2,3-g]isoquinoline;

(±)-trans-2-Benzylaminocarbonyl-3,6-dimethyl-8a-(3-hydroxyphenyl)-4,4a,5,6,7,8,8a,9-octahydro-1H-pyrrolo[2,3-g]isoquinoline hydrochloride;

(±)-trans-3,6-Dimethyl-8a-(3-methoxyphenyl)-2-pyrrolidinocarbonyl-4,4a,5,6,7,8,8a,9-octahydro-1H-pyrrolo[2,3-g]isoquinoline;

(±)-trans-3,6-Dimethyl-8a-(3-hydroxyphenyl)-2-pyrrolidinocarbonyl-4,4a,5,6,7,8,8a,9-octahydro-1H-pyrrolo[2,3-g]isoquinoline hydrochloride;

(±)-trans-6-Ethyl-3-methyl-8a-(3-methoxyphenyl)-2-phenylaminocarbonyl-4,4a,5,6,7,8,8a,9-octahydro-1H-pyrrolo[2,3-g]isoquinoline;

(±)-trans-6-Ethyl-8a-(3-hydroxyphenyl)-3-methyl-2-phenylaminocarbonyl-4,4a,5,6,7,8,8a,9-octahydro-1H-pyrrolo[2,3-g]isoquinoline;

(±)-trans-2-Diethylaminothiocarbonyl-6-ethyl-3-methyl-8a-(3-methoxyphenyl)-4,4a,5,6,7,8,8a,9-octahydro-1H-pyrrolo[2,3-g]isoquinoline;

(±)-trans-2-Diethylaminothiocarbonyl-6-ethyl-8a-(3-hydroxyphenyl)-3-methyl-4,4a,5,6,7,8,8a,9-octahydro-1H-pyrrolo[2,3-g]isoquinoline;

(±)-trans-6-Cyclopropylmethyl-2-diethylaminocarbonyl-8a-(3-methoxyphenyl)-3-methyl-4,4a,5,6,7,8,8a,9-octahydro-1H-pyrrolo[2,3-g]isoquinoline hydrochloride;

(±)-trans-6-Cyclopropylmethyl-2-diethylaminocarbonyl-8a-(3-hydroxyphenyl)-3-methyl-4,4a,5,6,7,8,8a,9-octahydro-1H-pyrrolo[2,3-g]isoquinoline hydrochloride;

(±)-trans-2-Diisopropylaminocarbonyl-6-ethyl-8a-(3-methoxyphenyl)-3-methyl-4,4a,5,6,7,8,8a,9-octahydro-1H-pyrrolo[2,3-g]isoquinoline;

(±)-trans-2-Diisopropylaminocarbonyl-6-ethyl-8a-(3-hydroxyphenyl)-3-methyl-4,4a,5,6,7,8,8a,9-octahydro-1H-pyrrolo[2,3-g]isoquinoline hydrochloride;

(±)-trans-2-Aminocarbonyl-6-ethyl-8a-(3-methoxyphenyl)-3-methyl-4,4a,5,6,7,8,8a,9-octahydro-1H-pyrrolo[2,3-g]isoquinoline;

(±)-trans-2-Aminocarbonyl-6-ethyl-8a-(3-hydroxyphenyl)-3-methyl-4,4a,5,6,7,8,8a,9-octahydro-1H-pyrrolo[2,3-g]isoquinoline hydrochloride;

(±)-trans-6-Ethyl-2-ethoxycarbonyl-8a-(3-methoxyphenyl)-4,4a,5,6,7,8,8a,9-octahydro-3-trifluoromethyl-1H-pyrrolo[2,3-g]isoquinoline;

(±)-trans-6-Ethyl-2-ethoxycarbonyl-8a-(3-hydroxyphenyl)-4,4a,5,6,7,8,8a,9-octahydro-3-trifluoromethyl-1H-pyrrolo[2,3-g]isoquinoline hydrochloride;

(±)-trans-2-Diethylaminocarbonyl-8a-(3-methoxyphenyl)-3-methyl-6-propyl-4,4a,5,6,7,8,8a,9-octahydro-1H-pyrrolo[2,3-g]isoquinoline hydrochloride;

(±)-trans-2-Diethylaminocarbonyl-8a-(3-hydroxyphenyl)-3-methyl-6-propyl-4,4a,5,6,7,8,8a,9-octahydro-1H-pyrrolo[2,3-g]isoquinoline hydrochloride;

(±)-trans-2-Dimethylaminocarbonyl-6-ethyl-8a-(3-methoxyphenyl)-3-methyl-4,4a,5,6,7,8,8a,9-octahydro-1H-pyrrolo[2,3-g]isoquinoline;

(±)-trans-2-Dimethylaminocarbonyl-6-ethyl-8a-(3-hydroxyphenyl)-3-methyl-4,4a,5,6,7,8,8a,9-octahydro-1H-pyrrolo[2,3-g]isoquinoline hydrochloride;

(−)-trans-2-Diethylaminocarbonyl-6-ethyl-8a-(3-methoxyphenyl)-3-methyl-4,4a,5,6,7,8,8a-octahydro-1H-pyrrolo[2,3-g]isoquinoline hydrochloride;

(−)-trans-2-Diethylaminocarbonyl-6-ethyl-8a-(3-hydroxyphenyl)-3-methyl-4,4a,5,6,7,8,8a,9-octahydro-1H-pyrrolo[2,3-g]isoquinoline hydrochloride;

(±)-trans-2-Diethylaminocarbonyl-6-ethyl-8a-(3-methoxyphenyl)-3-methyl-4,4a,5,6,7,8,8a-octahydro-1H-pyrrolo[2,3-g]isoquinoline hydrochloride;

(±)-trans-2-Diethylaminocarbonyl-6-ethyl-8a-(3-hydroxyphenyl)-3-methyl-4,4a,5,6,7,8,8a,9-octahydro-1H-pyrrolo[2,3-g]isoquinoline hydrochloride;

(±)-trans-2-Diethylaminocarbonyl-6-(2-furylmethyl)-8a-(3-methoxyphenyl)-3-methyl-4,4a,5,6,7,8,8a,9-octahydro-1H-pyrrolo[2,3-g]isoquinoline hydrochloride;

(±)-trans-2-Diethylaminocarbonyl-6-(2-furylmethyl)-8a-(3-hydroxyphenyl)-3-methyl-4,4a,5,6,7,8,8a,9-octahydro-1H-pyrrolo[2,3-g]isoquinoline;

(±)-trans-2-Diethylaminocarbonyl-8a-(3-methoxyphenyl)-3-methyl-4,4a,5,6,7,8,8a-octahydro-1H-pyrrolo[2,3-g]isoquinoline;

(±)-trans-6-Butyl-2-diethylaminocarbonyl-8a-(3-methoxyphenyl)-3-methyl-4,4a,5,6,7,8,8a-octahydro-1H-pyrrolo[2,3-g]isoquinoline;

(±)-trans-6-Butyl-2-diethylaminocarbonyl-8a-(3-hydroxyphenyl)-3-methyl-4,4a,5,6,7,8,8a-octahydro-1H-pyrrolo[2,3-g]isoquinoline;

(±)-trans-6-Ethyl-8a-(3-methoxyphenyl)-3-methyl-2-pyrrolidinocarbonyl-4,4a,5,6,7,8,8a,9-octahydro-1H-pyrrolo[2,3-g]isoquinoline hydrochloride;

(±)-trans-6-Ethyl-8a-(3-hydroxyphenyl)-3-methyl-2-pyrrolidinocarbonyl-4,4a,5,6,7,8,8a,9-octahydro-1H-pyrrolo[2,3-g]isoquinoline;

(±)-trans-2-Diisopropylaminocarbonyl-8a-(3-methoxyphenyl)-3-methyl-6-propyl-4,4a,5,6,7,8,8a-octahydro-1H-pyrrolo[2,3-g]isoquinoline hydrochloride, and (±)-trans-2-Diisopropylaminocarbonyl-8a-(3-hydroxyphenyl)-3-methyl-6-propyl-4,4a,5,6,7,8,8a-octahydro-1H-pyrrolo[2,3-g]isoquinoline hydrochloride.

7. A pharmaceutical composition comprising a compound according to claim of claims 1 to 6 and a pharmaceutically acceptable carrier.

8. A method for the treatment and/or prophylaxis of pain and of rejection of transplants and skin grafts in mammals, which comprises administering to the mammal in need of such treatment and/or prophylaxis an effective amount of a compound according to claim 1.

* * * * *